(12) United States Patent
Baier et al.

(10) Patent No.: US 9,084,417 B2
(45) Date of Patent: Jul. 21, 2015

(54) DELIVERY OF ETHYLENE BLOCKING AND/OR PROMOTING AGENTS

(71) Applicant: Dow AgroSciences LLC, Indianapolis, IN (US)

(72) Inventors: Gretchen Baier, Midland, MI (US); Mark D. Newsham, Sanford, MI (US); Irina V. Graf, Midland, MI (US); Robert L. Schmitt, Annandale, NJ (US); Lamy J. Chopin, III, Flemington, NJ (US); Jacquelyn A. deGroot, Lake Jackson, TX (US); Jeffrey J. Wooster, Houston, TX (US); Tarlochan Singh Dhadialla, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/100,843

(22) Filed: Dec. 9, 2013

(65) Prior Publication Data

US 2014/0094369 A1    Apr. 3, 2014

Related U.S. Application Data

(62) Division of application No. 12/523,423, filed as application No. PCT/US2008/051000 on Jan. 14, 2008, now Pat. No. 8,603,524.

(60) Provisional application No. 60/880,748, filed on Jan. 17, 2007.

(51) Int. Cl.
*A01N 25/10* (2006.01)
*A61K 9/26* (2006.01)
*A01N 27/00* (2006.01)
*C08K 5/01* (2006.01)
*A01N 43/24* (2006.01)
*A01N 43/90* (2006.01)

(52) U.S. Cl.
CPC ............... *A01N 25/10* (2013.01); *A01N 27/00* (2013.01); *A01N 43/24* (2013.01); *A01N 43/90* (2013.01); *C08K 5/01* (2013.01)

(58) Field of Classification Search
None
See application file for complete search history.

(56) References Cited

FOREIGN PATENT DOCUMENTS

EP          1593306        * 11/2005

* cited by examiner

*Primary Examiner* — Alton Pryor
(74) *Attorney, Agent, or Firm* — Osha Liang LLP

(57) ABSTRACT

A composition including an ethylene blocking agent complex formed from the product of an ethylene blocking agent and a host, and at least one water-soluble polymer, wherein the ethylene blocking agent complex and the at least one water-soluble polymer are intermingled is disclosed.

19 Claims, 2 Drawing Sheets

DELIVERY OF ETHYLENE BLOCKING AND/OR PROMOTING AGENTS

CROSS REFERENCE TO RELATED APPLICATIONS

This application is a divisional application and claims benefit under 35 U.S.C. §120 to U.S. patent application Ser. No. 12/523,423, filed Jul. 16, 2009, which will issue as U.S. Pat. No. 8,603,524, on Dec. 10, 2013, which is a National Stage of International Application PCT/US2008/51000, filed Jan. 14, 2008, which claims the benefit of U.S. Provisional Patent Application Ser. No. 60/880,748 filed Jan. 17, 2007. All of these applications are incorporated by reference in their entirety.

BACKGROUND OF INVENTION

1. Field of the Invention

Embodiments disclosed herein relate generally to delivery systems for ethylene blocking agents. More specifically, embodiments disclosed herein relate to compositions including ethylene blocking agent complexes and water-soluble or water-swellable polymers.

2. Background

Ethylene is an important regulator of the growth and development of plants, interacting with ethylene receptor proteins in plant tissues. In harvested fruits, vegetables, and ornamentals, ethylene may promote color development, ripening, stimulate dehiscence in nuts, promote flowering, and reduce lodging in cereals. Ethylene may also be produced by plants in biologically active amounts in response to various stresses, including drought, chilling, water-logging or flooding, anoxia, and various pathogens. Such stress associated production of ethylene is known to cause programmed cell death leading to the premature death of plants or plant parts, including, for example, flowers, leaves, fruits, and vegetables, through binding with certain ethylene receptors in the plant. Ethylene is also known to cause abscission of leaves and flowers during certain growth and stress conditions, and to promote leaf yellowing and stunted growth as well as premature fruit, flower, and leaf drop. In addition, ethylene is also known to induce or accelerate the ripening of harvested fruits and vegetables, which may result in excessive softening and increased susceptibility to pathogens. Because of these ethylene-induced effects, ways to control the effects of ethylene on plants are sought.

Current methods to control shelf-life of plants, fruits, and vegetables may include ethylene blocking agents (antagonists of ethylene action or its biosynthesis), as will be described in more detail below. Additionally, methods to control shelf-life that may be used in place of or in combination with ethylene antagonism include harvesting before peak ripeness, treating with inhibitors of membrane degrading phospholipases, (e.g., hexanal and lysophosphatidylethanolamine) cold storage, modified atmosphere packaging, packaging materials that minimize bruising, wax coatings on the product or packaging, ethylene scavengers, ethylene exposure to promote ripening, and direct genetic modification of the organism, among others.

U.S. Pat. No. 5,518,988 discloses the use of cyclopropene and its derivatives, including methylcyclopropene, as effective blocking agents for ethylene binding. However, a major problem with these compounds is that they are typically unstable gases which present explosive hazards when compressed.

U.S. Pat. No. 6,017,849 and EP1237411 disclose incorporation of these gaseous cyclopropenes into a molecular encapsulation agent complex in order to stabilize their reactivity and thereby provide a convenient and safe means of storing, transporting, and applying or delivering the active compounds to plants, avoiding the problems presented by the unstable gases. For the most effective cyclopropene derivative disclosed in U.S. Pat. No. 5,518,988, 1-methylcyclopropene ("1-MCP"), the preferred molecular encapsulation agent is a cyclodextrin, with alpha-cyclodextrin being the most preferred. The encapsulation of 1-MCP improves the stability of the product during transportation and storage by allowing the 1-MCP to be delivered in a powdered form and later activated by contacting the complex with gaseous or liquid water to release the 1-MCP gas. Thus, the application or delivery of these active compounds to plants is accomplished by simply adding water to the molecular encapsulation agent complex.

U.S. Pat. No. 6,313,068 discloses the encapsulation of longer chain cyclopropene derivatives in cyclodextrin, among other encapsulation agents. Also disclosed is the packaging of the 1-MCP complex, where the preferred package is made of polyvinyl alcohol. When the consumer is ready to use the complex, the consumer may dissolve the powder and the packet in an aqueous solution and expose the resulting solution to the plant.

U.S. Pat. No. 6,444,619 and EP1192859 indicate that the powder formulations suffer from a number of deficiencies including, for example, dustiness, difficulty in measuring small amounts (which may require that the material be pre-packaged), and difficulty in controlling the release of the encapsulated material from the powder, and that it would be advantageous to moderate the release of 1-MCP so that very little of it is released during the first few minutes after the complex is added to water. To overcome these deficiencies and to moderate the release of 1-MCP, U.S. Pat. No. 6,444,619 and EP1192859 disclose that the encapsulated 1-MCP may be pressure agglomerated to form tablets, wafers, pellets, briquettes, and similar forms.

U.S. Pat. No. 6,897,185 and WO2002024171 disclose the addition of an effervescent agent with a tablet form of the 1-MCP complex to speed the release of 1-MCP upon exposure to moisture. The effervescent action may facilitate the bursting of the tablet in an aqueous solvent, thereby promoting the release of 1-MCP. U.S. Pat. No. 6,762,153 and EP1304035 disclose improving the efficiency of the 1-MCP release by combining the 1-MCP complex with one or more carbon dioxide generating additives (a combination of acids and carbonates or bicarbonates, such as a combination of citric acid, sodium bicarbonate, and benzoic acid).

U.S. Patent Application Publication No. 2003220201 discloses a method for delivering cyclopropene gas to plants in an enclosed space. The delivery method comprises bubbling gas through a volume of water that contains a suspension of a cyclopropene/cyclodextrin complex. The bubbling action may provide the energy to liberate the cyclopropene from its carrier molecule and then facilitate transit of the cyclopropene from the water into the atmosphere.

U.S. Pat. No. 6,426,319 and EP1192858 disclose incorporation of a super-absorbent polymer (SAP) to the 1-MCP/cyclodextrin complex. The SAP may provide for a slow release of the cyclopropene from the encapsulating agent or may provide for release of the cyclopropene with only small amounts of water.

U.S. Pat. No. 6,548,448 and EP1236397 disclose incorporation of a cyclopropene derivative compound with a packaging material. The packaging materials may include cardboard and plastic containers, wooden boxes, paper bags, wax coatings, coated paper, plastic films, and adhesives. Plastic film compositions include polyethylene, ethyl vinyl acetate polymers, polyvinyl alcohol, and polystyrene. The packaging materials included either (a) a sachet/packet within which the 1-MCP complex was heat sealed, or (b) films exposed to 1-MCP vapor. When the 1-MCP was in the form of a complex, the 1-MCP was released by exposure to humidity, and when the 1-MCP was not in the form of a complex, the 1-MCP was released by simple diffusion.

WO2004101668 discloses a packaging film composition comprising a thermoplastic base, a filler, an ethylene response inhibitor, and a moisture transmitting material. The ethylene antagonist incorporated in the thermoplastic film is released via moisture from a plant contained in the package. The thermoplastic bases described include polyolefins, polycarbonates, polyamides, ethyl vinyl acetate and ethyl methyl acetate copolymers, and polysulfones, among others. Calcium carbonate was used as the filler, and polyethylene glycol was used as the moisture transmitting material.

U.S. Pat. No. 6,770,600 and EP1340425 disclose delivery substrates for the 1-MCP complex that can be plastic, paper, or fabric from natural or synthetic fibers. The release agent can be a gel, such as hydroxypropylmethylcellulose or polyvinylpyrrolidinone, coated onto paper, polypropylene, polyester, or polyethylene non-wovens or films. Water contact with the gel causes the release of 1-MCP which permeates through the porous substrate. The 1-MCP/cyclodextrin complex may be incorporated into hydrophilic gels applied as coatings, such as a tape. The tape may be pulled through a water chamber or exposed to moisture to release the 1-MCP. The hydrophilic gels of U.S. Pat. No. 6,770,600 and EP1340425 are applied as coatings to a non-soluble substrate, not to films that would dissolve upon exposure to sufficient water.

Other delivery methods include two-compartment systems, where water is provided in one compartment and the 1-MCP complex in the other. Upon breach of the separation between the two compartments, the contents mix to activate and release the 1-MCP.

The above described powders, tablets, and films may present handling issues, and may be slow to dissolve or may not controllably release the 1-MCP. Accordingly, there exists a need for more convenient, effective, and efficient ways to release and deliver 1-MCP.

SUMMARY OF INVENTION

In one aspect, embodiments disclosed herein relate to a composition including an ethylene blocking agent complex formed from the product of an ethylene blocking agent and a host, and at least one water-soluble polymer, wherein the ethylene blocking agent complex and the at least one water-soluble polymer are intermingled.

In one aspect, embodiments disclosed herein relate to a composition comprising an ethylene blocking agent complex comprising the product of an ethylene blocking agent and a host; and at least one degradable polymer; wherein the ethylene blocking agent complex and the at least one degradable polymer are intermingled.

In one aspect, embodiments disclosed herein relate to a dispersion comprising an ethylene blocking agent complex comprising the product of an ethylene blocking agent and a host; and at least one polymer selected from the group consisting of water-soluble polymers, water-swellable polymers, water-reactive polymers, photo-degradable polymers, phase-change materials, and UV-degradable polymers.

In one aspect, embodiments disclosed herein relate to a process of forming a structure incorporating an ethylene blocking agent comprising intermingling an ethylene blocking agent complex comprising the product of an ethylene blocking agent and a host with at least one thermally-processable water-soluble or photo-degradable polymer to form a composition, and processing the composition to form a structure.

In one aspect, embodiments disclosed herein relate to a method of exposing plants to an ethylene blocking agent, the method comprising placing a composition comprising an ethylene blocking agent complex and a degradable polymer proximate a plant exposing the degradable polymer to a condition that will effect the release an ethylene blocking agent from the ethylene blocking agent complex.

Other aspects and advantages of the invention will be apparent from the following description and the appended claims.

DETAILED DESCRIPTION

Figure 1:
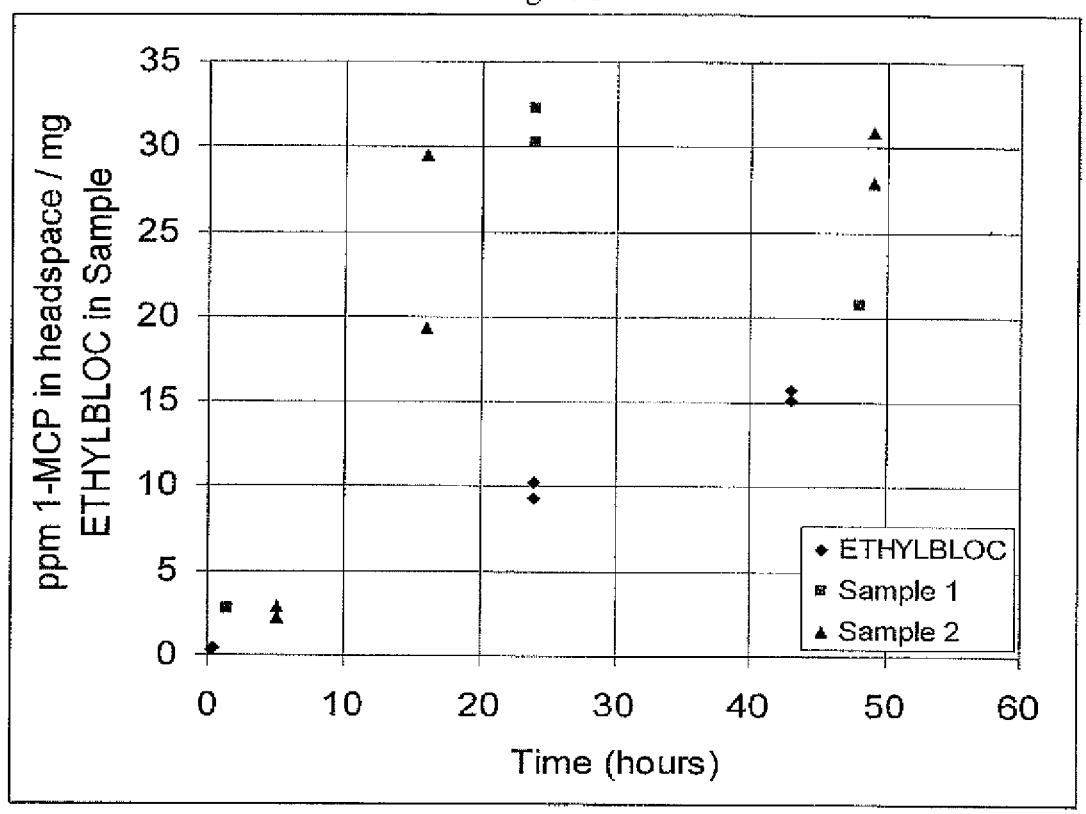
FIG. 1 graphically compares experimental results for release rates for films comprising 1-MCP according to embodiments disclosed herein to 1-MCP/alpha-cyclodextrin powders.

In one aspect, embodiments disclosed herein relate to compositions and structures useful for delivering ethylene blocking agents. In other aspects, embodiments disclosed herein relate to dispersions, froths, coatings, films, foams, and fibers comprising ethylene blocking agent complexes. In other aspects, embodiments disclosed herein relate to dispersions, froths, coatings, films, foams, and fibers or fibrous structures comprising ethylene blocking agent complexes and water-soluble or water-swellable polymers.

Some of the coatings, structures, and substrates useful in embodiments disclosed herein may be formed from dispersions, froths, and foams. For example, coatings or foams useful in embodiments may be formed from froths or frothed dispersions. As used herein, the terms "frothing" or "frothed" refers to a process where substantial volumes of air, or other gas, are incorporated in a liquid where, in some embodiments, at least 80 volume percent of the resulting composition (the frothed material) consists of the gaseous component. In other embodiments, at least 85 volume percent of the frothed material consists of the gaseous component; and at least 90 volume percent in yet other embodiments. The liquid may be a molecular solution, micellar solution, or dispersion in an aqueous or organic medium. In general the frothed liquid is created by mechanical methods such as high shear mixing under atmospheric conditions or optionally injecting gas into the system while mixing. The term "froth," as used herein, refers to a liquid which has been frothed, as described above, before drying or removing the liquid medium.

The term "foam," as used herein, refers to a resilient structure formed by removing a portion of the liquid medium from a froth, i.e., at least a portion, a substantial portion, or all of the liquid medium may be removed. As used herein, drying and removing may be used interchangeably, and may include thermal and/or mechanical removal of the liquid medium. The formation of foams from froths in accordance with embodiments disclosed herein may be described as follows. A froth may include pockets of vapor within a dispersion, where the dispersion includes polymer particles in a liquid medium. When the liquid medium is removed from the froth during a drying or removing process, the polymer particles may coalesce and melt together creating an interconnected film or struts around the entrapped vapor bubbles, giving stability to the resulting structure. Film formation may depend upon variables including the melting point of polymers within the froth, the rate of removal (i.e., evaporation rate) of the liquid medium, and overall froth composition, among others. For example, as water is removed from a froth formed from an aqueous dispersion, polymers contained in the dispersion may coalesce, forming a film, giving structure and resiliency to the resulting foam. In some embodiments, foams may be formed where the amount of residual liquid ranges from 0 to 20 weight percent; 0 to 10 weight percent in other embodiments; and 0 to 8 percent in yet other embodiments.

As described above, embodiments of the various structures and compositions containing or incorporating ethylene blocking additives may include various substrates, including fibers, films, non-wovens, fabrics, and foams. Coatings or structures may be formed from dispersions, froths, and foams, each of which may include additives such as dispersion stabilizing agents, frothing surfactants, and other additives. Additionally, embodiments of the coatings and structures disclosed herein include ethylene blocking agents and ethylene blocking agent complexes. Each of these components and methods to form the structures useful for delivering ethylene blocking agents disclosed herein are described in more detail below.

Ethylene Blocking Agents and Complexes Formed Therefrom

The ethylene blocking agent useful in embodiments disclosed herein for blocking the ethylene binding site in plants includes all the conventional compounds that inhibit ethylene responses in plants, such as, but not limited to cyclopentadiene, cyclopropene, diazocyclopentadiene, 1-methylcyclopropene, 3,3-dimethycyclopropene, methylenecyclopropane, trans-cyclooctene, cis-cyclooctene, 2,5-norbornadiene, and derivatives of the same. Ethylene blocking agents may also include the compounds that inhibit ethylene responses in plants disclosed in the following references, all of which are incorporated by reference: U.S. Pat. Nos. 3,879,188, 5,100, 462, 5,518,988, and 6,017,849, 6,313,068, 6,426,319, 6,444, 619, 6,548,448, 6,562,758, 6,762,153, 6,770,600, and 6,897, 185, PCT Patent Publication WO2004101668, and Sisler et al., Plant Growth Reg. 9, 157-164, 1990. In some embodiments, the agent for blocking the ethylene binding site in plants is 1-methylcyclopropene.

Derivatives of cyclopropene, cyclopentadiene, and diazocyclopentadiene may be represented by the following formulae (I), (II), and (III), respectively:

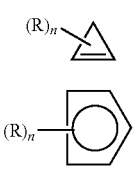

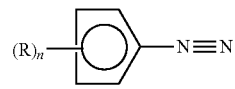

where n is an integer from 1 to 4. Suitable R groups may include hydrogen, saturated or unsaturated $C_1$ to $C_4$ alkyl, hydroxy, halogens, and $C_1$ to $C_4$ alkoxy, amino and carboxy. The term "alkyl" is defined herein to refer to linear or branched, saturated or unsaturated alkyl groups. Examples include but are not limited to methyl, ethyl, propyl, isopropyl and butyl.

In other embodiments, ethylene blocking agents may include inhibitors of ethylene biosynthesis, including aminoethoxyvinylglycine (the active ingredient of RETAIN (available from Valent Bio-Sciences). Inhibitors of ethylene biosynthesis may also include alpha-amino isobutyric acid, (aminooxy)acetic acid, methoxyvinylglycine, salicylic acid, and acetylsalicylic acid, among others.

In other embodiments, ethylene blocking agents may include agents that prevent the ripening of fruits and vegetables or the browning of cut fruits and vegetables, including inhibitors of fruit and vegetable membrane degrading phospholipases. Inhibitors of fruit and vegetable membrane degrading phospholipases may include hexanal, hisophosphatidylethanolamine, and their derivatives. Inhibitors of fruit and vegetable membrane degrading phospholipases may also include cytokines, such as N-(2-chloro-4-pyrridinyl)N-phenyl urea, an active ingredient of PRESTIGE (available from Valent Bio-Sciences).

The above described ethylene blocking agents, including compounds that inhibit the ethylene response in plants, compounds that inhibit ethylene biosynthesis, and phospholipase inhibitors, may be used alone, or in combinations of two or more, in compositions and structures described herein. Suitable agents are disclosed in, for example, U.S. Pat. Nos. 6,153,559; 6,514,914; 6,426,105; and 5,110,341, all of which are incorporated by reference in their entirety.

Many of the above described ethylene blocking agents may be gaseous, including 1-MCP. Complexes may be formed from the above described ethylene blocking agents to overcome instability, handling, and shelf-life issues, among others. For example, 1-MCP is a gas at room temperature and room pressure, and may be stabilized by complexation using various forms of host-guest chemistry, including, but not limited to, molecular encapsulation agents, inclusion compounds, intercalation compounds, clathrates, cryptands, molecular imprinted polymers (MIPS), and molecular tweezers, among others. Host-guest complexes formed using these and other forms of host-guest chemistry will be referred to herein as ethylene blocking agent complexes.

An ethylene blocking agent complex may be formed, in some embodiments, between a molecular encapsulation agent and the above described ethylene blocking agents, many of which may be gaseous. For example, 1-MCP is a gas at room temperature and room pressure, and may be stabilized by complexation with a solid carrier. Upon exposure of the ethylene blocking agent complex to moisture, the carrier may dissolve or undergo a conformational change, releasing the gaseous ethylene blocking agent. Methods for forming the ethylene blocking agent complexes useful in embodiments described herein may be found in several of the above given references relating to ethylene blocking agents.

A molecular encapsulation agent is a compound that may have a lock and key structure, similar to an enzyme, whereby a substrate selectively fits into the encapsulation site. In some embodiments, the molecular encapsulation agent may be alpha-cyclodextrin. In other embodiments, molecular encapsulation agents such as crown ethers, polyoxyalkylenes, prophorines, polysiloxanes, phosphazenes, and zeolites may also be used. In other embodiments, molecular encapsulation agents may include beta-cyclodextrin and gamma-cyclodextrin. The preferred complexing agent may vary depending upon the size of the R substituent, and one skilled in the art will appreciate that any mixture of encapsulating agents may be used. In certain embodiments, a complex formed between 1-MCP and alpha-cyclodextrin may be used.

In some embodiments of the compositions and structures incorporating the ethylene blocking agent complexes described herein, the ethylene blocking agent may be present in the ethylene blocking agent complex in an amount from 0.05 to 0.5 percent by weight; from 0.15 to 0.4 percent by weight in other embodiments; and from 0.2 to 0.35 percent by weight in yet other embodiments.

In other embodiments, complexation of the ethylene blocking agent may be accomplished using various clathrates, cage compounds, host-guest complexes, inclusion compounds, intercalation compounds, and adducts. These complexes may release an entrapped ethylene blocking agent above a temperature at which the complex becomes unstable in some embodiments. In other embodiments, intercalates may release an entrapped ethylene blocking agent upon dehydration, or when the intercalate falls below a given concentration of water.

In other embodiments, an ethylene blocking agent complex may be formed using molecular imprinted polymers (MIPS) or other biomimetic systems. MIPS may include polymers formed in the presence of a molecule that is extracted afterwards, thus leaving complementary cavities behind. Several polymer systems have been developed for use in molecular imprinting technology, including polyacrylate-based, polyacrylamide-based, polystyrene-based, and polysiloxane-based systems. These polymer-based MIPS systems may include functional comonomers including carboxylic acids (such as acrylic acid, methacrylic acid, vinylbenzoic acid), sulphonic acids (such as acrylamido-methylpropanesulphonic acid), and heteroaromatic (weak) bases (such as vinylpyrridine, vinylimidazole), an iminodiacetic acid derivative, and others. These polymer-based systems are commonly crosslinked to a very high degree (70-90%) to achieve molecular specificity, and crosslinkers may include isomers of divinylbenzene, ethylene glycol dimethacrylate (EDMA), trimethylolpropane trimethacrylate (TRIM), pentaerythritol triacrylate (PETRA), pentaerythritol tetraacrylate (PETEA), among others.

In yet other embodiments, the ethylene blocking agent may be encapsulated in a microballoon, microcapsule, or microsphere. The compound forming the micro-encapsulation may be wholly or partially water-soluble, water-swellable (including expansion due to osmotic-pressure), temperature unstable, thermally degradable, or combinations thereof, as described below, so as to release the ethylene blocking agent when a desired release condition is obtained or encountered. In other embodiments, the micro-encapsulation may be pressure sensitive. For example, the micro-encapsulation may be stable at high pressures, and whereupon application, such as by spraying a field, the micro-encapsulation becomes unstable at atmospheric pressures, releasing the ethylene blocking agent. In other embodiments, the ethylene blocking agent may be encapsulated in a vapor phase polymerization (VPP) glass coating that breaks down under physical stress. In other embodiments, the ethylene blocking agent may be contained in elastic fibers or elastic bicomponent fibers, where the ethylene blocking agent complex may be released or exposed upon stress or strain of the fibers. In other embodiments, the ethylene blocking agent may be encapsulated in microspheres or cells of closed-cell foams.

In various embodiments, components may be used for the controlled release or exposure of the ethylene blocking agents or complexes upon heating, chilling, water-logging or flooding, or drought conditions. In other embodiments, ethylene blocking agents or complexes may be exposed or released upon the sensing or detection of mineral depletion, insects (biosensors), various pheromones, pathogens, insect trails (such as the slime of a slug or snail), or the like.

In other embodiments, ethylene blocking agents and complexes may be imbibed in an ion exchange material or bead, natural zeolites, and artificial zeolites. Ion exchange materials may include resins such as crosslinked polystyrene, and may include functional groups including sulfonic acid groups (e.g., sodium polystyrene sulfonate or polyAMPS), trimethylammonium groups (e.g., polyAPTAC), carboxylic acid groups, and amino groups (e.g., polyethylene amine), among others.

As alluded to briefly above, it may be desired to effect release of ethylene blocking agents from compositions and structures incorporating the ethylene blocking agent or ethylene blocking agent complexes at desired times or under certain conditions, such as drought, flood, and others. It may also be desired to control or measure the release of the ethylene blocking agents. To result in the desired ethylene blocking agent release characteristics, the ethylene blocking agent or the ethylene blocking agent complex may be intermingled with one or more degradable or unstable compositions or polymers, including water-swellable, water-soluble, water-shrinkable, photo-degradable, UV-degradable, temperature-sensitive, or water-reactive compositions and polymers. In some embodiments, water-insoluble polymers may be used to control the release of ethylene blocking agents from the compositions and structures. In yet other embodiments, compositions including the ethylene blocking agent complexes may be formed into dispersions, froths, foams and other structures.

Degradable (or Unstable) Polymers

Compositions disclosed herein may include any water-soluble or water-swellable polymer. Water-soluble and water-swellable polymers useful in forming embodiments of the films and compositions disclosed herein may include cellulose-based polymers, such as methylcellulose (i.e. METHOCEL), hydroxyethyl cellulose (HEC) (i.e. CELLOSIZE), ethylcellulose (i.e. ETHOCEL), cationic HEC, and other cellulose derivatives. Polyoxyethylene (such as POLYOX) may also be used in some embodiments. Each of the above indicated trademarked products is available from The Dow Chemical Company, Midland, Mich.

Water soluble polymers and water-swellable polymers may also include hydroxypropylmethyl cellulose, hydroxypropyl cellulose, hydroxypropylmethyl cellulose phthalate, hydroxypropylmethyl cellulose acetate succinate, carboxymethylethyl cellulose, cellulose acetate phthalate, polyvinylacetal diethylaminoacetate, aminoalkyl methacrylate copolymer, hydroxypropylmethyl cellulose acetate succinate, methacrylic acid copolymers including methacrylic acid-methyl methacrylate copolymers, cellulose acetate trimellitate (CAT), polyvinyl acetate phthalate, shellac, carboxymethyl cellulose, calcium carboxymethyl cellulose, sodium carboxymethyl cellulose, croscarmellose sodium A-type (Ac-di-sol), starch, crystalline cellulose, hydroxypropyl starch, partly pregelatinized starch, polyvinylpyrrolidone, gelatin, gum arabic, ethyl cellulose, polyvinyl alcohol, pullulan, pregelatinized starch, agar, tragacanth, sodium alginate, propyleneglycol alginate, cellulose derivatives, starch derivatives, pectins, polyacrylates, polyvinyl acetate phthalate, oxidized regenerated cellulose, polyacrylates, modified starches (including water-soluble polymers derived from a starch (e.g., corn starch, potato starch, tapioca starch) such as by acetylation, halogenation, hydrolysis (e.g., such as which an acid), or enzymatic action, or any type of water-soluble modified starch, including but not limited to oxidized, ethoxyolated, cationic, lypophilic and pearl starch, may be used), polyvinyl alcohol, polyethylene glycols, natural and synthetic gums like guar gum, xanthan gum, cellulose gum, *acacia* gum, polycarbophil, polyolefin oxides such as polyethylene oxide, locust bean gum, bentonite, scheroglucan, polyacrylic acids such as carbopol, polycarbophil, poly(methyl vinyl ether-co-methacrylic acid), poly(2-hydroxyethyl methacrylate), poly(methylmethacrylate), poly(isobutylcyanoacrylate), poly(isohexyecyanoacrylate) and polydimethylaminoethyl methacrylate, hydrolytically unstable polyesters containing derivatizable groups, alginate, carrageenan, guar gum derivatives, karaya gum, dextran, hyaluronic acid, pullulan, amylose, high amylose starch, hydroxypropylated high amylose starch, dextrin, pectin, chitin, chitosan, levan, elsinan, collagen, gelatin, zein, gluten, soy protein isolate, polysaccharides, whey protein isolate, and casein. In other embodiments combinations of the above described water-soluble and water-swellable polymers may be used.

In other embodiments, compositions may include polymers that are reactive or break down in the presence of water. For example, compositions may include poly(lactic acid), poly(glycolic acid), or combinations thereof.

Suitable GRAS certified polymers for use in the water-soluble and water-swellable structures include poly(vinyl pyrrolidone), methyl cellulose, hydroxy propyl cellulose, poly(ethylene oxide), poly(acrylic acid), polyacrylates such as CARBOPOL 934, starch and starch derivatives, polysaccharides, sodium carboxymethyl cellulose, xanthan gum, karaya gum, and gelatin, among others.

In other embodiments, bio-degradable (including moisture, UV, or biologically degradable compositions), photo-degradable or UV-degradable compositions may be used. Photo-degradable and UV-degradable compositions may include homopolymers and copolymers of vinyl or vinylidene monomers such as polyethylene, polypropylene, polymethylpentene, polyvinlchloride, ethylene-propylene copolymers, polyamides, polyesters, polyurethanes, and interpolymers containing unsaturation, as well as mixtures of such polymers. The photo-degradable compositions may degrade very rapidly on exposure to the environment owing to the presence of particular metal complexes, including complexes of iron, manganese, cesium, nickel, cobalt, copper, and zinc. In some embodiments, photo-degrading agents may include heavy metal dithiocarbamates and dithiophosphates. In other embodiments, photo-degradable polymers may include ethylene-carbon monoxide (ECO) polymers. In some embodiments, photo-degradable compositions may include polymers having carbonyl groups and anatase titanium dioxide, such as disclosed in U.S. Pat. No. 5,286,786; U.S. Pat. No. 5,089,556; and U.S. Pat. No. 5,250,587, which are hereby fully incorporated by reference.

In other embodiments, thermally unstable or temperature sensitive compositions may be used. Thermally unstable compositions may include polymers such as partially aromatic amorphous polyamides, polycarbonate ethers, polyacrylonitriles, and cellulose triacetates. In other embodiments, temperature sensitive compositions may include phase change materials such as waxes, salt hydrides, fatty acids and esters, and paraffins. For example, if the temperature exceeds the melting point or decomposition point of a composition, an encapsulated ethylene blocking agent complex may be exposed, such as by high permeability zoned created in the composition or due to melting of the temperature-sensitive composition. Conversely, if the temperature falls, a temperature-sensitive composition may become solid again, preventing further release of the ethylene blocking agent. In various embodiments, a thermally unstable composition may undergo decomposition at or above temperatures from $-20°$ C. to $120°$ C. In various embodiments, a temperature sensitive composition may undergo a phase change at a temperature between $-20°$ C. and $120°$ C., wherein the ethylene blocking agent may be released or exposed due to the phase transition. The temperature at which the desired decomposition or phase change occurs may depend upon the environment for which the material will be exposed. For example, articles for use in tropical environments may have a higher decomposition or phase change temperature than articles for use in moderate or arctic environments due to the relative temperatures at which release of the ethylene blocking agent may be desired.

In other embodiments, any degradable polyelectrolyte can be used, including, but not limited to, hydrolytically degradable, biodegradable, thermally degradable, and photolytically degradable polyelectrolytes. Hydrolytically degradable polymers include for example, certain polyesters, polyanhydrides, polyorthoesters, polyphosphazenes, and polyphosphoesters. Biodegradable polymers include, for example, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Those skilled in the art will recognize that this is an exemplary, not comprehensive, list of biodegradable polymers. The properties of these and other polymers and methods for preparing them are further described in the art. See, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. Nos. 4,806,621; 4,638,045 to Kohn; and U.S. Pat. No. 4,946,929 to d'Amore; see also Wang et al., J. Am. Chem. Soc. 123:9480, 2001; Lim et at, J. Am. Chem. Soc. 123:2460, 2001; Langer, Acc. Chem. Res. 33:94, 2000; Langer, J. Control Release 62:7, 1999; and Uhrich et al., Chem. Rev. 99:3181, 1999. Of course, co-polymers, mixtures, and adducts of these polymers may also be used.

In other embodiments, bio-resins as well as cellulose and wood pulp based biodegradable polymers may be used. Such resins are available from, for example, Innovia Films, such as the NATUREFLEX family of polymers, and from Cereplast, including resin starch or polylactic acid based bio-resins.

In some embodiments, the ratio of degradable polymer to ethylene blocking agent complex may range from 20:1 to 1:10 by weight. In other embodiments, the ratio of degradable polymer to ethylene blocking agent complex may be from 9:1 to 1:1 by weight; and from 3:1 to 1:1 by weight in other embodiments. In other embodiments, the ratio of degradable polymer to ethylene blocking agent complex may be from 1:1 to 1:9; and from 1:1 to 1:3 in yet other embodiments.

In some embodiments, the ratio of water-soluble polymer to ethylene blocking agent complex may range from 20:1 to 1:10 by weight. In other embodiments, the ratio of water-soluble polymer to ethylene blocking agent complex may be from 9:1 to 1:1 by weight; and from 3:1 to 1:1 by weight in other embodiments. In other embodiments, the ratio of water-soluble polymer to ethylene blocking agent complex may be from 1:1 to 1:9; and from 1:1 to 1:3 in yet other embodiments.

In some embodiments, the ratio of water-swellable polymer to ethylene blocking agent complex may range from 20:1 to 1:10 by weight. In other embodiments, the ratio of water-swellable polymer to ethylene blocking agent complex may be from 9:1 to 1:1 by weight; and from 3:1 to 1:1 by weight in other embodiments. In other embodiments, the ratio of water-swellable polymer to ethylene blocking agent complex may be from 1:1 to 1:9; and from 1:1 to 1:3 in yet other embodiments.

In some embodiments, the ratio of photo-degradable polymer to ethylene blocking agent complex may range from 20:1 to 1:10 by weight. In other embodiments, the ratio of photo-degradable polymer to ethylene blocking agent complex may be from 9:1 to 1:1 by weight; and from 3:1 to 1:1 by weight in other embodiments. In other embodiments, the ratio of photo-degradable polymer to ethylene blocking agent complex may be from 1:1 to 1:9; and from 1:1 to 1:3 in yet other embodiments.

In some embodiments, the ratio of thermally-unstable polymer to ethylene blocking agent complex may range from 20:1 to 1:10 by weight. In other embodiments, the ratio of thermally-unstable polymer to ethylene blocking agent complex may be from 9:1 to 1:1 by weight; and from 3:1 to 1:1 by weight in other embodiments. In other embodiments, the ratio of thermally-unstable polymer to ethylene blocking agent complex may be from 1:1 to 1:9; and from 1:1 to 1:3 in yet other embodiments.

Water-Insoluble Polymers

Compositions and films disclosed herein may include water-insoluble polymers. Water-insoluble polymers useful in some embodiments may include homopolymers, copolymers, interpolymers and multi-block interpolymers of olefin monomers such as ethylene, propylene, 1-butene, 3-methyl-1-butene, 4-methyl-1-pentene, 3-methyl-1-pentene, 1-heptene, 1-hexene, 1-octene, 1-decene, and 1-dodecene, as typically represented by polyethylene, polypropylene, poly-1-butene, poly-3-methyl-1-butene, poly-3-methyl-1-pentene, poly-4-methyl-1-pentene, ethylene-propylene copolymer, ethylene-1-butene copolymer, and propylene-1-butene copolymer. In other embodiments, water-insoluble polymers may include copolymers (including elastomers) of an alpha-olefin with a conjugated or non-conjugated diene, as typically represented by ethylene-butadiene copolymer and ethylene-ethylidene norbornene copolymer; and polyolefins (including elastomers) such as copolymers of two or more alpha-olefins with a conjugated or non-conjugated diene, as typically represented by ethylene-propylene-butadiene copolymer, ethylene-propylene-dicyclopentadiene copolymer, ethylene-propylene-1,5-hexadiene copolymer, and ethylene-propylene-ethylidene norbornene copolymer; ethylene-vinyl compound copolymers such as ethylene-vinyl acetate copolymer, ethylene-vinyl alcohol copolymer, ethylene-vinyl chloride copolymer, ethylene acrylic acid or ethylene-(meth)acrylic acid copolymers, and ethylene-(meth) acrylate copolymer; styrenic copolymers (including elastomers) such as polystyrene, ABS, acrylonitrile-styrene copolymer, α-methylstyrene-styrene copolymer, styrene vinyl alcohol, styrene acrylates such as styrene methylacrylate, styrene butyl acrylate, styrene butyl methacrylate, and styrene butadienes and crosslinked styrene polymers; and styrene block copolymers (including elastomers) such as styrene-butadiene copolymer and hydrates thereof and styrene-isoprene-styrene tri-block copolymer; polyvinyl compounds such as polyvinyl chloride, polyvinylidene chloride, vinyl chloride-vinylidene chloride copolymer, polymethyl acrylate, and polymethyl methacrylate; polyamides such as nylon 6, nylon 6,6, and nylon 12; thermoplastic polyesters such as polyethylene terephthalate and polybutylene terephthalate; polycarbonate, polyphenylene oxide, and the like; and glassy hydrocarbon-based resins, including poly-dicyclopentadiene polymers and related polymers (copolymers, terpolymers); saturated mono-olefins such as vinyl acetate, vinyl propionate and vinyl butyrate and the like; vinyl esters such as esters of monocarboxylic acids, including methyl acrylate, ethyl acrylate, n-butylacrylate, isobutyl acrylate, dodecyl acrylate, n-octyl acrylate, phenyl acrylate, methyl methacrylate, ethyl methacrylate, and butyl methacrylate and the like; polyurethanes; acrylonitrile, methacrylonitrile, acrylamide, and mixtures thereof; resins produced by ring opening metathesis and cross metathesis polymerization and the like. These resins may be used either alone or in combinations of two or more.

Compositions containing ethylene blocking agents and the above described degradable and water-insoluble polymers may also be incorporated into a structure, such as non-woven, wovens, coated substrates, impregnated substrates, and the like. In some embodiments, compositions and substrates may include the above described polymers. In other embodiments, structures may be formed from natural or synthetic materials, including polyolefins, such as, polyethylene, polypropylene, polybutylene, and the like; polyesters, such as polyethylene terephthalate, poly(glycolic acid) (PGA), poly(lactic acid) (PLA), poly(β-malic acid) (PMLA), poly(ε-caprolactone) (PCL), poly(p-dioxanone) (PDS), poly(3-hydroxybutyrate) (PHB), and the like; polyamides, such as nylons (nylon-6, nylon-6,6, nylon-6,12, and others); polyaramids, such as KEVLAR®, NOMEX®, and the like, TEFLON, and polyester nylons (EP); cellulosic esters; cellulosic ethers; cellulosic nitrates; cellulosic acetates; cellulosic acetate butyrates; ethyl cellulose; regenerated celluloses, such as viscose, rayon, and the like; cotton; flax; silk; hemp; and mixtures thereof. In other embodiments, substrates may include polymers such as ethylene-vinyl acetate (EVA), ethylene/vinyl alcohol copolymers, polystyrene, impact modified polystyrene, ABS, styrene/butadiene block copolymers and hydrogenated derivatives thereof (SBS and SEBS), and thermoplastic polyurethanes. Suitable polyolefins may include linear or low density polyethylene, polypropylene (including atactic, isotactic, syndiotactic and impact modified versions thereof) and poly(4-methyl-1-pentene). Suitable styrenic polymers may include polystyrene, rubber modified polystyrene (HIPS), styrene/acrylonitrile copolymers (SAN), rubber modified SAN (ABS or AES) and styrene maleic anhydride copolymers. In other embodiments, substrates may include wood, metal, clays, plastics, and other materials commonly used for planting, potting, shipping, harvesting, crating, and supporting plants, fruits, vegetables, and the like.

Embodiments disclosed herein may also include a polymeric fiber that may include at least one multi-block olefin interpolymer. Suitable multi-block olefin interpolymers may include those described in U.S. Provisional Patent Application No. 60/818,911, for example. The term "multi-block copolymer" or "multi-block interpolymer" refers to a polymer comprising two or more chemically distinct regions or segments (referred to as "blocks") preferably joined in a linear manner, that is, a polymer comprising chemically differentiated units which are joined end-to-end with respect to polymerized ethylenic functionality, rather than in pendent or grafted fashion. In certain embodiments, the blocks differ in the amount or type of comonomer incorporated therein, the density, the amount of crystallinity, the crystallite size attributable to a polymer of such composition, the type or degree of tacticity (isotactic or syndiotactic), regio-regularity or regio-irregularity, the amount of branching, including long chain branching or hyper-branching, the homogeneity, or any other chemical or physical property.

As another suitable resin, the esterification products of a di- or poly-carboxylic acid and a diol comprising a diphenol may be used. These resins are illustrated in U.S. Pat. No. 3,590,000, which is incorporated herein by reference. Other specific examples of resins include styrene/methacrylate copolymers, and styrene/butadiene copolymers; suspension polymerized styrene butadienes; polyester resins obtained from the reaction of bisphenol A and propylene oxide followed by the reaction of the resulting product with fumaric acid; and branched polyester resins resulting from the reaction of dimethylterephthalate, 1,3-butanediol, 1,2-propanediol, and pentaerythritol, styrene acrylates, and mixtures thereof.

Further, specific embodiments of the present disclosure may employ ethylene-based polymers, propylene-based polymers, propylene-ethylene copolymers, and styrenic copolymers as one component of a composition. Other embodiments of the present disclosure may use polyester resins, including those containing aliphatic diols such as UNOXOL 3,4 diol, available from The Dow Chemical Company (Midland, Mich.).

In specific embodiments, polyolefins such as polypropylene, polyethylene, copolymers thereof, and blends thereof, as well as ethylene-propylene-diene terpolymers, may be used. In some embodiments, preferred olefinic polymers include homogeneous polymers, as described in U.S. Pat. No. 3,645,992 issued to Elston; high density polyethylene (HDPE), as described in U.S. Pat. No. 4,076,698 issued to Anderson; heterogeneously branched linear low density polyethylene (LLDPE); heterogeneously branched ultra low linear density polyethylene (ULDPE); homogeneously branched, linear ethylene/alpha-olefin copolymers; homogeneously branched, substantially linear ethylene/alpha-olefin polymers, which can be prepared, for example, by processes disclosed in U.S. Pat. Nos. 5,272,236 and 5,278,272, the disclosures of which are incorporated herein by reference; and high pressure, free radical polymerized ethylene polymers and copolymers such as low density polyethylene (LDPE) or ethylene vinyl acetate polymers (EVA).

Polymer compositions, and blends thereof, described in U.S. Pat. Nos. 6,566,446, 6,545,088, 6,538,070, 6,448,341, 6,316,549, 6,111,023, 5,869,575, 5,844,045, or 5,677,383, each of which is incorporated herein by reference in its entirety, may also be suitable in some embodiments. In some embodiments, the blends may include two different Ziegler-Natta polymers. In other embodiments, the blends may include blends of a Ziegler-Natta polymer and a metallocene polymer. In still other embodiments, the polymer used herein may be a blend of two different metallocene polymers. In other embodiments, single site catalyst polymers may be used.

In some embodiments, the polymer is a propylene-based copolymer or interpolymer. In some particular embodiments, the propylene/ethylene copolymer or interpolymer is characterized as having substantially isotactic propylene sequences. The term "substantially isotactic propylene sequences" and similar terms mean that the sequences have an isotactic triad (mm) measured by $^{13}$C NMR of greater than about 0.85 in one embodiment; greater than about 0.90 in another embodiment; greater than about 0.92 in another embodiment; and greater than about 0.93 in yet another embodiment. Isotactic triads are well-known in the art and are described in, for example, U.S. Pat. No. 5,504,172 and WO 00/01745, which refer to the isotactic sequence in terms of a triad unit in the copolymer molecular chain determined by $^{13}$C NMR spectra.

Some of the above described polyolefin polymers may be provided under various trade names, including VISTAMAXX, VISTALON, and EXXELOR, available from ExxonMobil Corp., and VERSIFY, INFUSE, AFFINITY, ENGAGE, ATTANE, PRIMACOR, ELITE, DOWLEX, INSPIRE, available from The Dow Chemical Co., Midland, Mich.

In some embodiments, the ratio of water-soluble polymer to water-insoluble polymer may range from 100:1 to 1:100 by weight. In other embodiments, the ratio of water-soluble polymer to water-insoluble polymer may range from 90:1 to 1:90 by weight; from 50:1 to 1:50 by weight in other embodiments; and from 10:1 to 1:10 in yet other embodiments.

Functionalized Polymers

The water-soluble, water-swellable, and water-insoluble polymers, copolymers, interpolymers, and multi-block interpolymers described above may be functionalized by incorporating at least one functional group in the polymer structure. Exemplary functional groups may include, for example, ethylenically unsaturated mono- and di-functional carboxylic acids, ethylenically unsaturated mono- and di-functional carboxylic acid anhydrides, salts thereof and esters thereof. Such functional groups may be grafted to a polymer, or may be copolymerized with additional comonomers to form an interpolymer including the functional comonomer and optionally other comonomer(s). Means for grafting functional groups are described, for example, in U.S. Pat. Nos. 4,762,890, 4,927,888, and 4,950,541, the disclosures of which are incorporated herein by reference in their entirety. One particularly useful functional group is maleic anhydride.

The amount of the functional group present in the functional polymer may vary. The functional group may be present in an amount of at least about 1 weight percent in some embodiments; at least about 5 weight percent in other embodiments; and at least about 7 weight percent in yet other embodiments. The functional group may be present in an amount less than about 40 weight percent in some embodiments; less than about 30 weight percent in other embodiments; and less than about 25 weight percent in yet other embodiments.

Additives:

The dispersions, froths, films, and compositions disclosed herein may include film-forming agents, plasticizing agents, surfactants (i.e., dispersion stabilizing agents, emulsifying agents, frothing surfactants), thickening agents, binding agents, effervescent ingredients and $CO_2$-forming additives, gel-forming agents, water-transmitting agents, super absorbent polymers, hydroscopic materials, and other additives. In other embodiments, the compositions disclosed herein may include other chemicals and compounds routinely applied to plants, including insecticides, herbicides, fungicides, fertilizers, growth factors, and the like.

Effervescent ingredient may be incorporated in embodiments of the compositions and films disclosed herein to control the release of the agent for blocking the ethylene binding site from the composition upon contact with water. Any reaction mixture which may generate an effervescent effect may be used, including a mixture of an alkaline compound and an acidic compound, which may be in solid form at room temperature. Acidic compounds may include tartaric acid, citric acid, fumaric acid, salicylic acid, oxalic acid, succinic acid, maleic acid, malic acid, glycolic acid, ornithuric acid, and gluconic acid. Alkaline compounds may include $NaHCO_3$, $KHCO_3$, $CaCO_3$, $Na_2CO_3$, $K_2CO_3$, $NaKCO_3$, sodium glycine carbonate, and the mixtures thereof. Upon contact of the compositions or films disclosed herein with water, the alkaline compound may react with the acidic compound to generate carbon dioxide gas.

Some embodiments of the compositions and films disclosed herein may also include plasticizers. Suitable GRAS certified plasticizers may include, for example, glycerin, sorbitol, any of the glycols, polysorbate 80, triethyl titrate, acetyl triethyl titrate, and tributyl citrate. In other embodiments, plasticizers may include triacetin, monoacetin, and diacetin.

Thickening agents may be used when it is desired to control the viscosity of the compositions and dispersions disclosed herein. Thickening agents may include natural products such as xanthan gums, or chemical agents such as polyacrylamide polymers and gels. In other embodiments, thickening agents may include methylcellulose, carboxyl methylcellulose, and the like. Suitable thickeners may also include ALCOGUM™ VEP-II (a trade designation of Alco Chemical Corporation) and PARAGUM™ 241 (a trade designation of Para-Chem Southern, Inc.). Other suitable thickeners may include cellulose derivatives such as METHOCEL™ products (a trade designation of The Dow Chemical Company). Thickening agents may also include natural products such as xanthan gums, or chemical agents such as polyacrylamide polymers and gels. Thickeners may be used in any amount necessary to prepare a dispersion of desired viscosity.

In certain applications, it may be desirable to increase the wettability of the compositions by adding surfactants. Examples of edible non-ionic surfactants that may be used include polyoxyethylene sorbitan fatty acid esters, polyoxyethylene alkyl ethers, and polyoxyethylene caster oil derivatives. An example of a suitable commercially available surfactant that may be used is polysorbate 80, which is a mixture of oleate esters of sorbitol and sorbitol anhydrides, consisting predominantly of the monoester, condensed with approximately 20 moles of ethylene oxide. A filler wetting agent may also be used in some embodiments. Useful filler wetting agents include phosphate salts such as sodium hexametaphosphate.

Surfactants used may include one or more nonionic surfactants. In some embodiments, surfactants may include mixtures of a polyoxyethylene sorbitan fatty acid ester, a polyoxyethylene alkyl ether, or a polyoxyethylene castor oil derivative with one or more polyalcohols. Polyalcohols may include propylene glycol, polyethylene glycol, or other polyalcohols commonly used in food, food service, cosmetic, or pharmaceutical products. In other embodiments, the mixture may include a polyoxyethylene sorbitan fatty acid ester and glycerol. Another combination of surfactants may include a first component such as a polyoxyethylene sorbitan fatty acid ester or an alpha-hydro-omega-hydroxypoly(oxyethylene) poly(oxypropylene)poly(oxyethylene) block copolymer, and a second component such as a polyoxyethylene alkyl ether or a polyoxyethylene castor oil derivative. In other embodiments, surfactants may include mono and diglycerides of fatty acids and polyoxyethylene sorbitol esters, such as, Atmos 300 and Polysorbate 80. Other suitable surfactants may include pluronic acid, sodium lauryl sulfate, and the like.

While starches may provide a film with an initial tortuosity level, the tortuosity of a film may be further increased and adjusted to a desired level by adding a water-soluble component such as sorbitol, a gel-former such as silicon dioxide, or liquids that are miscible with water, such as propylene glycol, glycerin, polyethylene-glycol sorbitan oleate, or the like.

Stabilizing agents useful in some embodiments may include xanthan gum, locust bean gum and carrageenan. Other suitable stabilizing agents may include guar gum and the like.

Emulsifying agents useful in some embodiments may include triethanolamine stearate, quaternary ammonium compounds, *acacia*, gelatin, lecithin, bentonite, veegum, and the like. Binding agents useful in some embodiments may include starches.

In other embodiments, coloring agents or color-change additives may be used. For example, colorants and color-change additives may be used such that the compositions and structures may be identified in situ (in soil, in packaging, etc.). In other embodiments, a color change may indicate that the ethylene blocking agent has been released from the compositions or structure.

Dispersions

Dispersions formed in accordance with embodiments disclosed herein may include a liquid medium, a polymer (water-soluble, water-swellable, and water-insoluble, alone or in combination), an ethylene blocking agent complex, a dispersion stabilizing agent, and optionally frothing surfactants, additives, and fillers.

Dispersions of the above described polymeric resins and ethylene blocking agent complexes may use a stabilizing agent to promote the formation of a stable dispersion or emulsion. In some embodiments, the dispersion stabilizing agent may be a surfactant, a polymer, or mixtures thereof. In other embodiments, the resin may be a self-stabilizer, such that an additional exogenous stabilizing agent may not be necessary. For example, a self-stabilizing system may include a partially hydrolyzed polyester, where by combining polyester with an aqueous base, a polyester resin and a surfactant-like stabilizer molecule may be produced. In particular, the stabilizing agent may be used as a dispersant, a surfactant for frothing the dispersion, or may serve both purposes. In addition, one or more stabilizing agents may be used in combination.

In certain embodiments, the dispersion stabilizing agent may be a polar polymer, having a polar group as either a comonomer or grafted monomer. In preferred embodiments, the stabilizing agent may include one or more polar polyolefins, having a polar group as either a comonomer or grafted monomer. Typical polymers include ethylene-acrylic acid (EAA) and ethylene-methacrylic acid copolymers, such as those available under the trademarks PRIMACOR™ (trademark of The Dow Chemical Company), NUCREL™ (trademark of E.I. DuPont de Nemours), and ESCOR™ (trademark of ExxonMobil) and described in U.S. Pat. Nos. 4,599,392, 4,988,781, and 5,938,437, each of which is incorporated herein by reference in its entirety. Other suitable polymers include ethylene ethyl acrylate (EEA) copolymer, ethylene methyl methacrylate (EMMA), and ethylene butyl acrylate (EBA). Other ethylene-carboxylic acid copolymer may also be used. Those having ordinary skill in the art will recognize that a number of other useful polymers may also be used.

If the polar group of the polymer is acidic or basic in nature, the dispersion stabilizing polymer may be partially or fully neutralized with a neutralizing agent to form the corresponding salt. The salts may be alkali metal or ammonium salts of the fatty acid, prepared by neutralization of the acid with the corresponding base, e.g., NaOH, KOH, and $NH_4OH$. These salts may be formed in situ in the dispersion step, as described more fully below. In certain embodiments, neutralization of the dispersion stabilizing agent, such as a long chain fatty acid or EAA, may be from 25 to 200% on a molar basis; from 50 to 110% on a molar basis in other embodiments. For example, for EAA, the neutralizing agent is a base, such as ammonium hydroxide or potassium hydroxide, for example. Other neutralizing agents may include lithium hydroxide or sodium hydroxide, for example. Those having ordinary skill in the art will appreciate that the selection of an appropriate neutralizing agent depends on the specific composition formulated, and that such a choice is within the knowledge of those of ordinary skill in the art.

Other dispersion stabilizing agents that may be used include long chain fatty acids or fatty acid salts having from 12 to 60 carbon atoms. In other embodiments, the long chain fatty acid or fatty acid salt may have from 12 to 40 carbon atoms.

Additional dispersion stabilizing agents include cationic surfactants, anionic surfactants, or non-ionic surfactants. Examples of anionic surfactants include sulfonates, carboxylates, and phosphates. Examples of cationic surfactants include quaternary amines. Examples of non-ionic surfactants include block copolymers containing ethylene oxide, propylene oxide, butylene oxide, and silicone surfactants. Surfactants useful as a dispersion stabilizing agent may be either external surfactants or internal surfactants. External surfactants are surfactants that do not become chemically reacted into the polymer during dispersion preparation. Examples of external surfactants useful herein include salts of dodecyl benzene sulfonic acid and lauryl sulfonic acid salt. Internal surfactants are surfactants that do become chemically reacted into the polymer during dispersion preparation. An example of an internal surfactant useful herein includes 2,2-dimethylol propionic acid and its salts or sulfonated polyols neutralized with ammonium chloride.

In particular embodiments, the dispersion stabilizing agent may be used in an amount ranging from greater than zero to about 60% by weight based on the total amount of the ethylene blocking agent complex and polymers (water-soluble, water-swellable, and water-insoluble) used. With respect to the polymers and the dispersion stabilizing agent, in some embodiments, the polymers may comprise from 30% to 99% (by weight) of the total amount of polymer, ethylene blocking agent complex, and dispersion stabilizing agent in the composition. In other embodiments, the polymer may comprise between about 50% and about 80% (by weight) of the total amount of polymer, ethylene blocking agent complex, and dispersion stabilizing agent in the composition. In yet other embodiments, the thermoplastic resins may comprise about 70% (by weight) of the total amount of polymer, ethylene blocking agent complex, and dispersion stabilizing agent in the composition. For example, long chain fatty acids or salts thereof may be used from 0.5 to 10% by weight based on the amount of polymer and ethylene blocking agent complex. In other embodiments, ethylene-acrylic acid or ethylene-methacrylic acid copolymers may be used in an amount from 0.5 to 60% by weight based on the amount of the polymer and ethylene blocking agent complex. In yet other embodiments, sulfonic acid salts may be used in an amount from 0.5 to 10% by weight based on the amount of polymer and ethylene blocking agent complex.

As discussed above, more than one dispersion stabilizing agent may be used, and combinations may be used as a dispersion stabilizing agent and as a frothing surfactant, for example. One of ordinary skill in the art will recognize that the dispersants used to create a relatively stable dispersion may vary depending on the nature of the polymers (water-soluble, water-swellable, and water-insoluble) employed.

The polymer, the ethylene blocking agent complex, and the dispersion stabilizing agent may be dispersed in a liquid medium. The liquid medium may include polar mediums, such as water, alcohols, aldehydes, ketones, chlorinated hydrocarbons, and the like. The liquid medium may also include non-polar mediums, such as linear, branched, or cyclic hydrocarbons, for example, including hexane, heptane, pentane, benzene, toluene, and the like.

In some embodiments, sufficient base is added to neutralize the resultant dispersion to achieve a pH range of about 6 to about 14. In particular embodiments, sufficient base is added to maintain a pH between about 9 to about 12. The liquid medium content of the dispersion may be controlled so that the combined content of the polymer (water-soluble, water-swellable, and water-insoluble), ethylene blocking agent complex, and the dispersion stabilizing agent (combined referred to as "solids content") is between about 1% to about 74% by volume. In another embodiment, the solids content ranges between about 25% to about 74% by volume. In yet another embodiment, the solid content ranges between about 30% to about 50% by weight. In yet another embodiment, the solids content ranges between about 40% to about 55% by weight.

Dispersions formed in accordance with some embodiments may be characterized in having an average particle size of between about 0.3 to about 5.0 microns. In other embodiments, dispersions may have an average particle size of from about 0.8 to about 1.2 microns. "Average particle size" as used herein refers to the volume-mean particle size. In order to measure the particle size, laser-diffraction techniques may be employed for example. A particle size in this description refers to the diameter of the polymer in the dispersion. For polymer particles that are not spherical, the diameter of the particle is the average of the long and short axes of the particle. Particle sizes can be measured on a Beckman-Coulter LS230 laser-diffraction particle size analyzer or other suitable device.

In a specific embodiment, a polymer (water-soluble, water-swellable, and water-insoluble), an ethylene blocking agent complex, and a dispersion stabilizing agent are melt-kneaded in an extruder along with the liquid medium and, if needed, a neutralizing agent, such as ammonia, potassium hydroxide, or a combination of the two, to form a dispersion compound. Those having ordinary skill in the art will recognize that a number of other neutralizing agents may be used. In some embodiments, one or more fillers may be added after blending the components.

Any melt-kneading means known in the art may be used. In some embodiments, a kneader, a BANBURY® mixer, single-screw extruder, or a multi-screw extruder may be used. A process for producing the dispersions in accordance with the present disclosure is not particularly limited. One preferred process, for example, is a process comprising melt-kneading the above-mentioned components according to U.S. Pat. No. 5,756,659 and U.S. Patent Publication No. 20010011118.

An extrusion apparatus that may be used in embodiments of the disclosure may be described as follows. An extruder, in certain embodiments a twin screw extruder, may be coupled to a back pressure regulator, melt pump, or gear pump. Desired amounts of polymer and ethylene blocking complex may be provided to the extruder from a solids hopper. Desired amounts of base and initial liquid medium may be provided to the extruder from a base reservoir and an initial liquid medium reservoir, respectively. Any suitable pump may be used, but in some embodiments a pump that provides a flow of about 150 cc/min at a pressure of 240 bar may be used to provide the base and the initial liquid medium to the extruder. In other embodiments, a liquid injection pump may provide a flow of 300 cc/min at 200 bar or 600 cc/min at 133 bar. In some embodiments, the base and initial liquid medium are preheated in a preheater. The components are melt-kneaded in the extruder to form the dispersion.

In producing the dispersion, the dispersion stabilizing surfactants are generally added to the dispersion along with other desired additives when viscosity is low and good mixing may be obtained. The dispersion stabilizing agents should then be added followed by any inorganic fillers, slowly enough to ensure good dispersion and avoid clumping/lumping of the filler. Finally a thickener may be added to obtain the desired viscosity.

Froths

The above described dispersions may be frothed in some embodiments. For preparing froths from the above described dispersions, a gaseous frothing agent is generally used. Examples of suitable frothing agents include: gases and/or mixtures of gases such as, for example, air, carbon dioxide, nitrogen, argon, helium. In some embodiments, an ethylene blocking agent, such as 1-MCP, may be used as a gas for frothing. Frothing agents are typically introduced by introduction of a gas at or above atmospheric pressure into a dispersion to form a homogeneous froth by mechanical shear forces during a predetermined residence time. In preparing the froths, it is preferred to mix all components of the dispersion and then blend the gas into the mixture.

The amount of air or other gas (where a gas in addition to or other than air is desirable) that may be incorporated in the froth may comprise at least 80% by volume in one embodiment, at least 85% by volume in another embodiment, and at least 90% by volume of the resultant froth in yet another embodiment. Initially, all components to be used in making the froth may be mixed together with mild agitation to avoid entrapping air.

Once all of the ingredients are well mixed, the mixture may be exposed to high shear mechanical mixing. During this step, the bulk viscosity of the mixture may increase as more air is entrapped within the continuous aqueous phase until a non-flowable, stiff froth is formed. The mixing time necessary to obtain froths of a desired density may vary with amount and type of froth stabilizing surfactant and the amount of mechanical shear. Any mechanical mixing device capable of whipping air into a thickened aqueous dispersion, such as a kitchen blender/hand mixer, Hobart mixer fitted with a wire whip, or, on a larger scale, a COWIE & RIDING™ Twin Foamer (Cowie Riding Ltd.), or equipment such as an OAKES™ or FIRESTONE® frother may be used. The commercial foamers may also allow one to inject air into their high shear mixing head to obtain very low (less than 50 g/L) density froth. In commercial frothers, air can be added directly into the mixing head to assist in development of low density froth. The speed of the frothing device may be increased or decreased to attain a desired froth density.

Froths that comprise the above described polymers and ethylene blocking agent complexes may also be formed as disclosed in PCT Application PCT/US2004/027593, filed Aug. 25, 2004, and published as WO2005/021622. In other embodiments, the polymers may also be crosslinked by any known means, such as the use of peroxide, electron beam, silane, azide, gamma irradiation, ultraviolet radiation, or other cross-linking techniques. The polymers may also be chemically modified, such as by grafting (for example by use of maleic anhydride (MAH), silanes, or other grafting agent), halogenation, amination, sulfonation, or other chemical modification.

Surfactants useful for preparing froths are referred to herein as frothing surfactants. A frothing surfactant may promote the formation of a stable froth, and may allow the gas used in frothing to disperse homogenously and efficiently into the formulated dispersion. The frothing surfactant may aid in the production of a non-sudsing composite foam product after drying.

Creating and stabilizing the froth during the frothing and drying steps may be accomplished by addition of a froth stabilizing surfactant to the dispersion when initially creating the froth. In addition, these surfactants may also be used to improve wetting of dried foams, if desired. Suitable frothing surfactants may be selected from cationic, nonionic and anionic surfactants. In some embodiments, frothing surfactants may include the dispersion stabilizing agents as described above.

In some embodiments, the frothing surfactant may be an alkylcellulose ethers, hydroxyalkyl cellulose ethers, hydroxyalkyl alkylcellulose ethers, guar gum, xanthan gum, and polyoxyethylene resins of at least 20,000 molecular weight, or combinations thereof. Other suitable frothing surfactants may be selected from cationic surfactants, anionic surfactants, or non-ionic surfactants. Examples of cationic surfactants include quaternary amines, primary amine salts, diamine salts, and ethoxylated amines. Examples of non-ionic surfactants include block copolymers containing ethylene oxide, silicone surfactants, alkylphenol ethoxylates, and linear and secondary alcohol ethoxylates of alkyl group containing more than 8 carbon atoms.

Examples of cationic surfactants include quaternary amines, primary amine salts, diamine salts, and ethoxylated amines. Examples of non-ionic surfactants include block copolymers containing ethylene oxide, silicone surfactants, alkylphenol ethoxylates, and linear and secondary alcohol ethoxylates of alkyl group containing more than 8 carbon atoms.

Examples of anionic surfactants include sulfonates, carboxylates, and phosphates. In one embodiment, anionic surfactants useful in preparing the froth from the aqueous dispersion may be selected from carboxylic acid salts and ester amides of carboxylic fatty acids, preferably fatty acids comprising from 12-36 carbon atoms, e.g., stearic or lauric acid, palmitic, myristic, oleic, linoleic, ricinoleic, erucic acid and the like.

In some embodiments, the surfactant may include amphoteric surfactants such as aminopropionates, amphoteric sulfonates, betaines, imidazoline based amphoterics, and sultaines, among others. For example, the surfactant may be derived from an imidazoline and can either be the acetate form (containing salt) or the propionate form (salt-free). Examples of suitable amphoteric surfactants include surfactants such as lauramidopropyl betaine, sodium laurimino dipropionate, cocoamidopropyl hydroxyl sultaine, alkylether hydroxypropyl sultaine, sodium capryloampho hydroxypropyl sulfonate, disodium capryloampho dipropionate, sodium cocoamphoacetate, disodium cocoamphodiacetate, sodium cocoamphopropionate, disodium octyl iminodipropionate, sodium cocoampho hydroxypropyl sulfonate, disodium lauryl iminodipropionate, sodium stearoampho acetate, and disodium tallow iminodipropionate, among others. Other amphoteric surfactants known in the art may also be used.

In some embodiments, the frothing surfactant may be used in an amount such that the resulting froth, as described below, may contain from 0.01 to 10.0 weight percent frothing surfactant based on the dry weight of the polymer. In other embodiments, the froth may contain from 0.02 to 3.0 weight percent frothing surfactant based on the dry weight of the polymer; from 0.03 to 2.5 weight percent based on the dry weight of the polymer in other embodiments; and from 0.05 to 10.0 weight percent based on the dry weight of the polymer in yet other embodiments. In various other embodiments, the frothing surfactant may be present in the froth in an amount ranging from a lower bound of 0.01, 0.02, 0.03, 0.04, or 0.05 weight percent based on the dry weight of the polymer to an upper bound of 2.0, 2.5, 3.0, 4.0, 5.0, or 10.0 weight percent based on the dry weight of the polymer, in any combination of given upper and lower bounds.

In addition to the above listed frothing surfactants, other surfactants may be used which do not detrimentally affect the frothing or stability of the froth. In particular additional anionic, zwitterionic or nonionic surfactants may be used in combination with the above listed surfactants.

Structures

The compositions including water-soluble and/or water-swellable polymers and an ethylene blocking agent complex, optionally with one or more water-insoluble polymers and other additives, described herein may be formed into various structures, such as films, dispersions, froths, foams, fibers, powders, flakes, pellets, or the like. In some embodiments, the structures may be formed by compression molding, extrusion, injection molding, blow molding, dry spinning, melt spinning, wet spinning, solution casting, spray drying, solution spinning, film blowing, calendering, rotational molding, powder injection molding, thixomolding, and other various methods to form films, foams, fibers, powders, flakes, pellets, pipe, tubes, and other desirable structures.

For example, in some embodiments, a film may be prepared by forming a coating solution, coating it onto a suitable carrier material, drying it, and cutting it into pieces of a size and shape suitable for the intended application of the film. In some embodiments, the liquid medium used to form the coating solution may be acceptable for food, food service, cosmetic, and pharmaceutical products. Examples, without limitation, of compatible liquid media include water, ethyl alcohol, isopropyl alcohol, or mixtures thereof. The solution may be coated onto a suitable substrate, dried, and cut into pieces of a size and shape suitable for the intended application. A variety of coating methods, such as Meyer rod, knife over roll, gravure, or reverse roll may be used to coat and oven-dry the film. Suitable substrates include non-siliconized kraft-paper, non-siliconized polyethylene-terephthalate film, non-siliconized polyethylene film, or the like. Depending upon the intended application and the desired properties of the final product, the thickness of the film may vary. The thickness may depend on the concentration of solids (water-soluble polymers, water-swellable polymers, water-insoluble polymers, and ethylene blocking agent complex) in the coating solution, the gap on the coating head, and the web speed. Film thickness may vary between 10 and 250 microns in some embodiments; between 100 and 1000 microns in other embodiments. In other embodiments, sheets may be formed, where the thickness may range from 0.01 to 3.0 cm. The dry films or sheets may be cut into pieces that are suitable for the intended application. The techniques to cut the dry films or sheets are known to the expert and may include roller dies, flat-bed cutting knives, or the like.

In other embodiments, the compositions including water-soluble and/or water-swellable polymers and an ethylene blocking agent complex, optionally with one or more water-insoluble polymers and other additives, described herein may be extruded into sheets or films, or may be formed into blown films, fibers, froths, foams, fibers, powders, flakes, pellets, extrusion coatings, or the like. Discrete structures, such as pellets, flakes, and powders, are advantageous for use in applications requiring a measurable or controllable dosage of the ethylene blocking agent. Films and sheets may also provide measurable and controllable dosage due to the ability of the user to select a desired length of film or sheet. Additionally, discrete structures may be advantageous for various disbursal methods, such as where the pellets are scattered throughout a field during planting or prior to harvesting, for example.

Substrates

In other embodiments, the compositions including water-soluble and/or water-swellable polymers and an ethylene blocking agent complex, optionally with one or more water-insoluble polymers and other additives, described herein may be coated on, impregnated in, disposed on, contained in, or intermingled with various substrates. The compositions may form or be contained in an outer layer of a multi-layer structure in some embodiments. The compositions may form or be contained in an inner layer or core of a multi-layer structure in other embodiments. The compositions may form or be contained in fibers or a portion of fibers that may be used to form a fibrous web in yet other embodiments.

In some embodiments, the substrates described herein may be formed from the above described water-soluble, water-swellable, and water-insoluble polymers. In other embodiments, the substrates may include the surfaces of seeds, plants, fruits, vegetables, grasses, cereals, nuts, vines, rice, and the like, for which ethylene inhibition is desired. In other embodiments, substrates may include the dirt or soil in which the plants are rooted. In other embodiments, substrates may include mulch, solid fertilizers, STYROFOAM (commonly used to "fluff" potting soil), or other solid components typically added to soil or used as ground cover. In yet other embodiments, substrates may include tresses, pots, containers, crates, films, and other materials commonly used to grow, support, store, package, or ship plants, fruits, vegetables, grasses, cereals, nuts, vines, rice, and the like, for which ethylene inhibition may be desired. In other embodiments, substrates may include films, cloths, fabrics, and weed-control fabrics commonly placed on, above, or in the ground in which the above described plants are grown.

In other embodiments, substrates may include sands, other mineral grains, pebbles, and other structures commonly found in soil. For example, the above described compositions including polymers and ethylene blocking agent complexes may be used to coat sand. These polymer coated sands may then be easily disbursed over a field or added to a container or pot, for example.

In some embodiments, substrates may include films and/or woven, knitted, and non-woven fibrous webs. In other embodiments, the substrates may be formed from, impregnated with, or coated with the above mentioned dispersions and froths.

In some embodiments, the substrates may be formed from fibers such as synthetic fibers, natural fibers, or combinations thereof. Synthetic fibers include, for example, polyester, acrylic, polyamide, polyolefin, polyaramid, polyurethane, regenerated cellulose, and blends thereof. Polyesters may include, for example, polyethylene terephthalate, polytriphenylene terephthalate, polybutylene terephthalate, polylatic acid, and combinations thereof. Polyamides may include, for example, nylon 6, nylon 6,6, and combinations thereof. Polyolefins may include, for example, propylene based homopolymers, copolymers, and multi-block interpolymers, and ethylene based homopolymers, copolymers, and multi-block interpolymers, and combinations thereof. Polyaramids may include, for example, poly-p-phenyleneteraphthalamid (KEVLAR®), poly-m-phenylencteraphthalamid (NOMEX®), and combinations thereof. Natural fibers may include, for example, wool, cotton, flax, and blends thereof.

The substrate may be formed from fibers or yarns of any size, including microdenier fibers and yarns (fibers or yarns having less than one denier per filament). The fabric may be comprised of fibers such as staple fiber, filament fiber, spun fiber, or combinations thereof. The substrate may be of any variety, including but not limited to, woven fabric, knitted fabric, non-woven fabric, or combinations thereof.

Substrates that may be used in embodiments disclosed herein may include woven or non-woven, natural or synthetic, components, fibers, films, foams, and fabrics. Non-wovens may include elastic non-wovens and soft non-wovens. In other embodiments, substrates may include fabrics or other textiles, porous films, and other non-wovens, including coated substrates. In certain embodiments, the substrate may be a soft textile, such as a soft or elastic non-woven, such as an elastomeric polyolefin or a polyurethane, for example. Wovens and/or knits made from microdenier fibers may also provided the desired substrate performance.

In some embodiments, the non-wovens may be based on polyolefin mono-component fibers, such as polyethylene or polypropylene. In other embodiments, bicomponent fibers may be used, for example where the core is based on a polypropylene and the sheath may be based on polyethylene. It should be understood that the fibers used in embodiments of the substrate may be continuous or non-continuous, such as staple fibers.

In other embodiments, suitable elastic non-wovens may be formed from one or more "elastomeric" polymers. The term "elastomeric" generally refers to polymers that, when subjected to an elongation, deform or stretch within their elastic limit. For example, spun-bonded fabrics formed from elastomeric filaments typically have a root mean square average recoverable elongation of at least about 75% based on machine direction and cross direction recoverable elongation values of the fabric after 30% elongation of the fabric and one pull. Advantageously, spun-bonded fabrics formed from elastomeric filaments typically have a root mean square average recoverable elongation of at least about 65% based on machine direction and cross direction recoverable elongation values of the fabric after 50% elongation of the fabric and one pull.

In other embodiments, apertured films may be utilized as a layer(s) of the composite structures or laminates described herein. Use of apertured films may increase the strength of the structure. Additionally the apertured films may provide for a through-thickness path through which water and the ethylene blocking agent, once released, may diffuse. Descriptions of apertured films may be found in WO200080341A1 and U.S. Pat. Nos. 3,929,135 and 4,324,246. Apertured films may include thin polymeric films with small openings spaced uniformly across the width of the film.

Embodiments of the structures incorporating an ethylene blocking agent complex may be formed by coating or impregnating a substrate with dispersions, froths, or foams formed from the polymers and ethylene blocking agent complexes described above. The polymeric compositions, dispersions, froths, and foams containing an ethylene blocking agent complex may be applied to a substrate via rolling, spray coating, brushing, casting, or other coating techniques. In other embodiments, coatings may be formed by coating a substrate with froths or foams formed from the above described dispersion.

When coating substrates in accordance with the present disclosure, the froths or dispersions containing the ethylene blocking agent complexes may be applied to the substrate topically or may be incorporated into the substrate by being pre-mixed with the fibers that are used to form the substrate. For instance, in one embodiment, the dispersion may be sprayed onto the substrate. When the dispersion containing the ethylene blocking agent complexes is applied to the substrate, the dispersion may be uniformly applied over the surface area of the web or may be applied according to a particular pattern.

When topically applied to a substrate, the ethylene blocking agent composition may be sprayed onto the substrate, extruded onto the substrate, or printed onto the substrate. When extruded onto the substrate, any suitable extrusion device may be used, such as a slot-coat extruder or a melt blown dye extruder. When printed onto the substrate, any suitable printing device may be used. For example, an inkjet printer or a rotogravure printing device may be used.

The dispersion containing the ethylene blocking agent complexes may be incorporated at any point in the substrate manufacturing process. The point during the process at which the dispersion is incorporated into the substrate may depend upon the desired end properties of the product. For example, the dispersions may be incorporated by direct addition of the dispersion to a fibrous slurry, such as by injection of the dispersion into a slurry. When combined with the fibrous slurry, a retention aid may also be present within the dispersion.

In other embodiments, a dispersion or froth spray may be applied to a substrate or a fibrous web substrate. For example, spray nozzles may be mounted over a moving web to apply a desired dose of the dispersions or froths to a fibrous web. Nebulizers may also be used to apply a light mist of the dispersion to a surface of a substrate web. In other embodiments, spray nozzles may be used to apply a desired dose of the dispersions or froths to substrates including plants.

In other embodiments, the dispersion may be printed onto a substrate, such as by offset printing, gravure printing, flexographic printing, ink jet printing, digital printing of any kind, and the like. In other embodiments, the dispersion may be coated onto one or both surfaces of a substrate, such as by blade coating, air knife coating, short dwell coating, cast coating, and the like. In some embodiments, a coating or printing containing an ethylene blocking agent complex may be selectively removed from portions of a coated structure.

In other embodiments, the dispersion may be extruded onto the surface of a paper web. For example, extrusion of dispersions is disclosed in PCT publication, WO 2001/12414, published on Feb. 22, 2001, herein incorporated by reference to the extent that it is non-contradictory herewith.

In other embodiments, the dispersion may be applied to individualized fibers used to form a substrate. For example, comminuted or flash dried fibers may be entrained in an air stream combined with an aerosol or spray of a dispersion containing a degradable polymer and an ethylene blocking agent complex to treat individual fibers prior to incorporation into a non-woven or other fibrous product.

In other embodiment, the dispersion may be heated prior to or during application to a paper web. Heating the composition may lower the viscosity for facilitating application. For instance, the dispersion may be heated to a temperature of from about 50° C. to about 150° C.

In other embodiments, a substrate may be impregnated with a solution or slurry, wherein the dispersion penetrates a significant distance into the thickness of the substrate, such as at least about 20% of the thickness of the web, more specifically at least about 30% and most specifically at least about 70% of the thickness of the web, including completely penetrating the web throughout the full extent of its thickness.

In other embodiments, the dispersion may be applied to a substrate using a foam application (e.g., foam finishing), either for topical application or for impregnation of the dispersion into the substrate under the influence of a pressure differential (e.g., vacuum-assisted impregnation of the foam). Principles of foam application of additives such as binder agents are described in U.S. Pat. Nos. 4,297,860 and 4,773,110.

In still other embodiments, the dispersion may be applied by padding of a solution of the dispersion compound into an existing substrate. Roller fluid feeding of the dispersion compound for application to the substrate may also be used.

In other embodiments, application of the dispersion compound by spray or other means to a moving substrate, belt, or fabric which in turn contacts the substrate to apply the dispersion to the substrate, such as is disclosed in PCT publication, WO 01/49937 by S. Eichhorn, "A Method of Applying Treatment Chemicals to a Fiber-Based Planar Product Via a Revolving Belt and Planar Products Made Using Said Method," published on Jun. 12, 2001.

In other embodiments, the dispersion may be applied after the substrate has been manufactured. That is, a dispersion formed in accordance with embodiments of the present invention may be added to a prior formed product, as by a paper converter for example. Dispersions may be incorporated, coated, or impregnated during an "in-line process," that is during the manufacturing of the substrate, or in an off-line application.

In some embodiments, polymeric sheets may be formed by extrusion coating, where the dispersion or froth containing the ethylene blocking agent complex may be extruded directly onto the desired substrate.

In other embodiments, the polymeric sheets may be formed by roll coating (doctor blade). The dispersion or froth may be applied to a continuous belt of substrate using a doctor blade a fixed height above the substrate. Dispersion or froth continuously fed to one side of the blade creates a constant pool of material. The moving substrate below the blade pulls from this pool of material with the thickness of the resultant coating to be fixed by the blade height. Additional layers of substrate or foam may be added as required. The resultant structure may then be dried to remove moisture and to aid in adhesion.

In other embodiments, sheets coated with the ethylene blocking agent complexes may be formed by spray coating. The dispersion or froth may be sprayed onto a desired substrate and subsequently dried.

In other embodiments, the polymeric sheets may be formed by curtain coating. The dispersion or froth may be applied via direct deposition onto a moving belt or substrate. The coating thickness is controlled by the dispersion or froth feed rate and the speed of the substrate below the curtain.

In other embodiments, the sheets containing ethylene blocking agent complexes may be formed by batch application. The dispersions or froths may be manually applied to a substrate surface. The surface may then be leveled using a knife blade and metering bars of desired thickness. The knife moves across the metering bars removing excess coating material from the surface creating a uniform height.

Additional processing techniques may include thermoforming, embossing, hydroentanglement, air lacing, exposure to infrared heat, and addition of surface fibers, such as flocking techniques.

After the dispersion or froth is applied to a substrate, the material may be treated in such a manner to remove substantially all of the water present in the dispersion or the froth, resulting in a coated or impregnated substrate. Removal of the water is generally done by use of a suitable energy source such as an infrared oven, a conventional oven, microwave or heating plates. Drying can be at ambient temperature, or in an oven at temperatures from 50° C. to 200° C. The amount of dispersion or froth used to coat or impregnate a textile may vary widely, depending on the characteristics of the textile, the type of ethylene blocking agent complex, the type of polymers used, and the desired coating weight and thickness.

In one embodiment, the coatings and foams described herein may be prepared from the dispersions or froths by removing at least a portion of the liquid/aqueous element of the dispersion or froth. In other embodiments, coatings may be prepared from the dispersions or froths by removing at least a majority of the liquid/aqueous element of the froth. In yet other embodiments, the coatings may be prepared by removing substantially the entire liquid/aqueous element. In various embodiments, greater than 30 weight percent, greater than 50 weight percent, greater than 80 weight percent, greater than 90 weight percent, greater than 95 weight percent, greater than 98 weight percent, or greater than 99 weight percent of the liquid/aqueous element may be removed. In one embodiment, the dispersions or froths may be dried by heating in a forced air drying oven, at temperatures selected for optimum drying. In one embodiment, the dispersion or froth coated substrate may be heated to a temperature between about 60° and 120° C. In some embodiments, foams are formed upon drying of the froths.

As the nature of the polymers used in the compositions containing ethylene blocking agent complexes permits, processing may be conducted at the highest temperature feasible to remove water as rapidly as possible from the dispersion or froth without destroying the viscosity of the polymer or polymer mixture, and without causing significant (e.g., more than 30 volume percent) collapse of the partially dried froth. In another embodiment, the drying temperature may be selected so as to not exceed the melting point temperature of the polymer or polymer mixture. In one embodiment, it may be desirable to dry the dispersions or froths at a temperature that approaches, but does not exceed the melting range of the polymers or polymer mixtures. In another embodiment, it may be desirable to attain a temperature where the amorphous regions in the polymeric resin begin to coalesce while pseudo-crosslinking with the substrate.

Some embodiments of the coating may have an average thickness ranging from about 0.05 mm to 10 mm or more; from about 0.1 mm to 6 mm in other embodiments; and from 0.2 mm to 2.5 mm in yet other embodiments. Other embodiments of the coating may have an average thickness ranging from 0.05 mm to 2.0 mm; and from 1 to 1.5 mm in yet other embodiments. Articles comprising embodiments of the coating may include at least one layer of coating having an average thickness ranging from 0.1 cm to 2.5 cm; from 0.5 cm to 2.0 cm in other embodiments; and from 1.0 cm to 1.5 cm in yet other embodiments. In other embodiments, one or more coatings may be laminated to a substrate, such as a nonwoven or a polymeric film.

Drying of the dispersions and froth to form the desired coatings may be conducted in batch or continuous mode. Devices including, for example, conventional forced air drying ovens or banks of infrared heating lamps or dielectric heating devices, e.g., radio (typically operated at permitted frequency bands in the range between 1-100 MHz) and microwave (typically operated at permitted frequency bands in the range between 400 to 2500 MHz) frequency energy generating sources, lining a tunnel or chamber in which the dispersion froth may be placed or conveyed through, in a continuous fashion, may be employed for drying. A combination of such drying energy sources may be used, either simultaneously or sequentially applied, to dry a froth or dispersion to form a coating. In one embodiment, the drying may include the simultaneous use of a dielectric device and a forced air drying oven. The temperature of the drying operation may be selected according to the nature and the melting range of the polymer (as determined by DSC) employed to prepare the coating. The dielectric heating frequency bands, permitted for industrial use in various countries, are designated in greater detail in the reference "Foundations of Industrial Applications of Microware and Radio Frequency Fields," Rousy, G and Pierce, J. A. (1995). In some embodiments, vacuum-assisted drying may be used, such as where the ethylene blocking agent complex or the degradable composition or polymer is temperature sensitive, for example.

In some embodiments, the substrate may be a porous or apertured non-woven substrate, where the pore space may transmit water and the released ethylene blocking agent. In other embodiments, the substrate or non-woven may be calendared, providing a path for through-thickness transmission.

Ethylene blocking agent complexes and the above described polymers may also be incorporated into multi-component or bi-component fibers. Multi-component or bicomponent fibers may include fibers that have one or more distinct polymer regions or domains encapsulating or containing one or more regions that include a composition comprising the ethylene blocking agent complex. The polymer and ethylene blocking agent complex containing regions may be arranged in substantially distinct zones across the cross-section of the multi-component or bicomponent fibers, and usually extend continuously along the length of the bicomponent fiber. In some embodiments, an interior of the multi-component fibers may include a composition including an ethylene blocking agent complex, and an outer region of the multi-component fiber may include one or more of the above described water-swellable, water-soluble, and water-insoluble polymers.

The configuration of a multi-component or bicomponent fiber may be, for example, a sheath/core arrangement, an "islands-in-the sea" arrangement, a side-by-side arrangement, or other configurations for multi- or bicomponent fibers, such as those described in U.S. Pat. Nos. 6,225,243, 6,140,442, 5,382,400, 5,336,552 and 5,108,820.

Any process which provides for the extrusion of multi-component fibers and filaments, such as that set forth in U.S. Pat. No. 5,290,626, may be used to form the multi-component fibers useful in embodiments described herein. Methods for making multi-component fibers are well known and need not be described here in detail. Generally, the multi-component fibers may be prepared using conventional multi-component textile fiber spinning processes and apparatus and utilizing mechanical drawing techniques as known in the art. Processing conditions for the melt extrusion and fiber-formation may vary depending upon the polymers used to form the fibers, and may be determined by those skilled in the art. Bicomponent fibers may be formed in some embodiments by melt-blowing or meltspinning processes.

The overall diameter of fibers used in embodiments disclosed herein may be widely varied. The fiber denier, however, may be adjusted to suit the capabilities of the finished article. Fiber diameter may be measured and reported in a variety of fashions. Generally, fiber diameter is measured in denier per filament. Denier is a textile term which is defined as the grams of the fiber per 9000 meters of that fiber's length. Monofilament generally refers to an extruded strand having a denier per filament greater than 15, usually greater than 30. Fine denier fiber generally refers to fiber having a denier of about 15 or less. Microdenier (or microfiber) generally refers to fiber having a diameter not greater than about 100 micrometers. Fibers useful in embodiments disclosed herein may include fibers having a diameter corresponding to monofilament, fine denier, and microdenier fibers. In some embodiments, the fiber diameter may range from about 0.5 to about 20,000 denier/filament. The sheath thickness, core diameter, or thickness of intermediate layers may be selected based upon the desired filament diameter or denier as well as the desired ethylene blocking agent release characteristics.

The shape of the fiber is not limited. For example, in some embodiments the fibers may have a circular or elliptical cross-sectional shape. In other embodiments, the fibers may have different shapes, such as a trilobal shape, or a flat (i.e., "ribbon" like) shape. The multi-component fibers disclosed herein are not limited by the shape of the fiber.

In other embodiments, the compositions containing an ethylene blocking agent complex and the above described water-soluble, water-swellable, and water-insoluble polymers described above may be used to form multi-component films and foams. Suitable films and foams may also be formed from the polymers used to form the above described fibers. Similar to the fiber forming process, multi-layer foams, films, and microcapillary films may be formed by co-extruding a compositions containing an ethylene blocking agent complex and at least one polymer. A multilayered film may be formed, for example, where an interior or exterior layer of the multi-layered film structure includes the compositions containing an ethylene blocking agent complex. In some embodiments, a composition containing an ethylene blocking agent complex may be sandwiched between two polymeric layers, forming a multi-layered sheet.

Release Characteristics

The rate of release of the ethylene blocking agent from the structures disclosed herein may be controlled in various manners, as known to those skilled in the art. The rate of release may be affected, for example, by varying the concentration of the ethylene blocking agent or ethylene blocking agent complex within the compositions and structures disclosed herein, by varying the thickness or aspect ratio of a water-soluble film comprising the ethylene blocking agent complex, by varying molecular weights of the various polymers used in the structures, or by varying the ratio of hydrophilic to hydrophobic polymers used in the compositions and structures. In other embodiments, the rate of release may be influenced by the amount of UV-degradable or thermally unstable polymers, drought-activated agents, water transmitting or absorbing agents, effervescent ingredients, and other additives.

The rate of release or amount of release in some embodiments may also be controlled by selecting a desired size of the structures disclosed herein. For example, a user may select a shorter length of film or fabric containing the ethylene blocking agent complex for a smaller release of ethylene blocking agent, or a longer length for a greater release of ethylene blocking agent. In other embodiments, the rate of release may be influenced based upon the rate in which the water-soluble or water-swellable components used in forming the structures described herein dissolve or swell in water. In other embodiments, the rate of release may be affected by the rate at which water diffuses through the structure and the location of the ethylene blocking agent complex within the structure.

In some embodiments, an initial release of the ethylene blocking agent may be obtained within seconds or minutes of the structures disclosed herein contacting water or occurrence of other degradation or release events. In other embodiments, an initial release of the ethylene blocking agent may be delayed for several hours. In other embodiments, an initial release of the ethylene blocking agent may be delayed for several days, weeks, or months from the time of delivery of the structure to the designated release area, such as where release is premised upon drought or flood conditions. In some embodiments, controlled release of ethylene blocking agents upon occurrence of a release event may be obtained by varying the polymer properties, thicknesses, concentrations, and other variables mentioned above and known to those skilled in the art.

Various applications for which ethylene blocking agents may be used may require different amounts of ethylene blocking agent dosing. As described above, structures and films described herein may advantageously provide for selective dosing. Other applications may require different doses of ethylene blocking agent to be delivered at various times. Structures and compositions described herein may provide for various modes of degradation, allowing for multiple releases or multiple release rates. For example, structures may provide for an initial release of ethylene blocking agent upon contact with water, and a second release of ethylene blocking agent upon UV-degradation. In some embodiments, compositions and structures disclosed herein may provide an initial burst or high-concentration release of ethylene blocking agent, followed by a low-concentration release over time. In other embodiments, compositions and structures disclosed herein may provide an initial low-concentration release over time, followed by a high-concentration release at a given time or condition.

In some embodiments, structures incorporating ethylene blocking agent complexes disclosed herein may have multiple release times. For example, structures may include one composition that includes a water-soluble polymer and an ethylene blocking agent complex, and another composition that includes a photo- or UV-degradable polymer and an ethylene blocking agent complex. As another example, films or multi-component fibers may include multiple layers having different activation mechanisms.

In other embodiments, structures incorporating ethylene blocking agent complexes disclosed herein may have multiple release rates. For example, structures may include two compositions having water-soluble polymers, where the water-soluble polymers have different degrees of water solubility.

In other embodiments, structures incorporating ethylene blocking agent complexes may have layers or sections comprising differing concentrations of water-insoluble polymers, water-permeabilities, additive concentrations (including effervescent ingredients and water-transmitting ingredients such as SAPs), aperturing, calendering, aspect ratios, or differences in other properties that may influence release rates of ethylene blocking agent from the composition.

Ethylene Generating Agents

In some embodiments, compositions and structures disclosed herein may include ethylene generating agents. Ethylene generating agents, such as ethephon, may be used to promote ripening, fruit coloring, and others effects as described above with respect to ethylene responses.

Ethylene generating agents or ethylene generating agent complexes may be incorporated into the compositions and structures disclosed herein. For example, a multi-component structure, such as a multi-layered film or a multi-component fiber, may include ethylene blocking agents in one layer and ethylene generating agents in another layer. In this manner, controlled release mechanisms, as described above, may allow ethylene blocking agents to be provided when the effects of ethylene are desired to be inhibited, and ethylene generating agents may be provided when the ripening or coloring of the fruits is desired, for example.

Accordingly, in certain embodiments it is contemplated that combinations of controlled-released blocking agents and generating agents may be used, in combination with various degradable polymers. For example, in one embodiment, ethylene blocking agents may be placed in a UV degradable polymer, while ethylene generating agents may be placed in a water degradable polymer, so that while exposed to light, a plant would not ripen or grow, but once water was added, growth/ripening would resume.

End-Uses

In addition to various uses disclosed above, films and other structures or substrates disclosed herein containing ethylene blocking agent complexes may be used as an inner liner in packaging materials, may be inserted into a container such as a sachet would be, may be used as an alternative to current warehouse fumigation delivery methods (typically a tablet thrown into a bucket of water). Dispersions and froths disclosed herein may be sprayed or distributed through irrigation systems, used to keep golf courses green, put into banana shrouds during harvest, may be delivered through crop dusters, and others. In other embodiments, the compositions may be used to increase flower drop at a desired stage so as to prevent the need for de-heading. In other embodiments, gloves or other apparatuses for picking or harvesting may be impregnated with compositions containing ethylene blocking agent complexes such that the further ripening of the harvest is at least partially inhibited.

Films and structures disclosed herein incorporating an ethylene blocking agent complex may be used to prevent numerous ethylene responses, such as those disclosed in U.S. Pat. Nos. 5,518,988 and 3,879,188. Ethylene responses may be initiated by either exogenous or endogenous sources of ethylene. Ethylene responses include, for example, the ripening and/or senescence, of flowers, fruits and vegetables; the abscission of foliage, flowers and fruit; the ripening and/or shortening of the life of ornamentals, such as potted plants, cut flowers, shrubbery and dormant seedlings; the inhibition of growth in some plants such as the pea plant; and the stimulation of plant growth in some plants such as the rice plant.

Vegetables that may be treated to inhibit senescence include leafy green vegetables such as lettuce (e.g., *Lactuea sativa*), spinach (*Spinaca oleracea*) and cabbage (*Brassica oleracea*; various roots such as potatoes (*Solanum tuberosum*), carrots (*Daucus*); bulbs such as onions (*Allium* sp.); herbs such as basil (*Ocimum basilicum*), oregano (*Origanum vulgare*) and dill (*Anethum graveolens*); as well as soybean (*Glycine max*), lima beans (*Phaseolus limensis*), peas (*Lathyrus* sp.), corn (*Zea mays*), broccoli (*Brassica oleracea italica*), cauliflower (*Brassica oleracea botrytis*) and asparagus (*Asparagus Officinalis*).

Fruits that may be treated to inhibit ripening include tomatoes (*Lycopersicon esculentum*), apples (*Malus domes tica*), bananas (*Musa sapientum*), pears (*Pyrus communis*), papaya (*Carica papya*), mangoes (*Mangifera indica*), peaches (*Prunus persica*), apricots (*Prunus anneniaca*), nectarines (*Prunus persica nectarina*), oranges (*Citrus* sp.), lemons (*Citrus limonia*), limes (*Citrus aurantifolia*), grapefruit (*Citrus paradisi*), tangerines (*Citrus nobilis deliciosa*), kiwi (*Actinidia Chinenus*), melons such as cantaloupes (*C. cantalupensis*) and musk melons (*C. melo*), pineapples (*Aranae comosus*), persimmon (*Diospyros* sp.) and raspberries (e.g., *Fragaria* or *Rubus ursinus*), blueberries (*Vaccinium* sp.), green beans (*Phaseolus vulgaris*), members of the genus *Cucumis* such as cucumber (*C. sativus*) and avocados (*Persea Americana*).

Ornamental plants that may be treated to inhibit senescence and/or to prolong flower life and appearance (such as the delay of wilting), include potted ornamentals and cut flowers. Potted ornamentals and cut flowers which may be treated with the methods of the present invention include azalea (*Rhododendron* spp.), hydrangea (*Macrophylla* hydrangea), hibiscus (*Hibiscus rosasanensis*), snapdragons (*Antirrhinum* sp.), poinsettia (*Euphorbia pulcherima*), cactus (e.g., *Cactaceae schlumbergera truncata*), begonias (*Begonia* sp.), roses (*Rosa* sp.), tulips (*Tulipa* sp.), daffodils (*Narcissus* sp.), petunias (*Petunia Hybrida*), carnation (*Dianthus caryophyllus*), lily (e.g., *Lilium* sp.), gladiolus (*Gladiolus* sp.), Alstroemeria (*Alstroemeria brasiliensis*), anemone (e.g., Anemone bland), columbine (*Aquilegia* sp.), aralia (e.g., *Aralia chinesis*), aster (e.g., *Aster carolinianus*), bougainvillea (*Bougainvillea* sp.), camellia (*Camellia* sp.), bellflower (*Campanula* sp.), cockscomb (*Celosia* sp.), falsecypress (*Chamaecyparis* sp.), chrysanthemum (*Chrysanthemum* sp.), clematis (*Clematis* sp.), cyclamen (*Cyclamen* sp.), freesia (e.g., *Freesia refracta*), and orchids of the family Orchidaceae.

Plants that may be treated to inhibit abscission of foliage, flowers and fruit include cotton (*Gossypium* Spp.), apples, pears, cherries (*Prunus avium*), pecans (*Carva illinoensis*), grapes (*Vitis vinifera*), olives (e.g., *Olea europaea*), coffee (*Cofffea arabica*), snapbeans (*Phaseolus vulgaris*), and weeping fig (*Ficus benjamina*), as well as dormant seedlings such as various fruit trees including apple, ornamental plants, shrubbery, and tree seedlings.

In other embodiments, compositions disclosed herein may be used to deliver ethylene blocking agents to marine or oceanic flora. For example, ethylene blocking agents may be used in kelp farming, to control the growth of algae, and with other various marine or oceanic plant varieties.

In other embodiments, compositions disclosed herein may be used to deliver ethylene blocking agents to grains and grasses, including prairie grasses, ornamental grasses, lawn grasses, seed and cereal grains and grasses, and other types of grains and grasses. Grains and grasses may include rye, wheat, rice, oats, barley, bahiagrass (*Papsalum Notatum*), bentgrass, Bermudagrass, bluestem, bluegrama, buffalograss, carpetgrass, centipedegrass, chewings fescue, creeping red fescue, gramagrass, indiangrass, hard fescue, Kentucky Bluegrass, perennial ryegrass, St. Augustinegrass, tall fescue, switchgrass, zoysiagrass, bromegrass, Canary grass, orchardgrass, feather reed grass (Calamagrostis varieties), blue fescues, Indian rice grass (*Oryzopsis hymenoides*), Blue oat grass (*Helictotrichon sempervirens*), June grass (*Koeleria macrantha* or *K. cristata*), silky threadgrass (*Nassella tenuissima*), pampas grasses (*Cortaderia* sp.), *Miscanthus* species, fountain grasses (*Pennisetum* sp.), variegated bulbous oat grass (*Arrhenatherum elatius bulbosum* 'Variegatum'), Rush family members (*Juncus* sp.), the cattail family (*Typha* sp.), and others.

In addition, shrubbery that may be treated to inhibit abscission of foliage include privet (*Ligustrum* sp.), photinea (*photina* sp.), holly (*Ilex* sp.), ferns of the family polypodiaceae, schefflera (*Schefflera* sp.), aglaonema (*Aglaonema* sp.), cotoneaster (*Cotoneaster* sp.), barberry (*Berberris* sp.), waxmyrtle (*Myrica* sp.), abelia (*Abelia* sp.), acacia (*Acacia* sp.), and bromeliades of the family Bromeliaceae.

EXAMPLES

Sample 1: POLYOX WSR N80 polymer (a non-ionic water-soluble poly(ethylene oxide) available from The Dow Chemical Co., Midland, Mich.) in a powdered form, having a specified solution viscosity by Brookfield viscometer of 65-115 cPs at 5%, was dry blended with ETHYLBLOC (a powder form of a complex of 1-MCP with alpha-cyclodextrin, containing approximately 0.14 weight percent 1-MCP, available from FLORALIFE, Inc.) in a 3:1 weight ratio. The resulting powder was compression molded at 140° C. to form a film, from which 11 mm×30 mm strips were cut, resulting in approximately 10 mg ETHYLBLOC per strip.

Sample 2: POLYOX WSR N80 polymer (a non-ionic water-soluble poly(ethylene oxide) available from The Dow Chemical Co., Midland, Mich.) in a powdered form was dry blended with ETHYLBLOC (a powder available from FLORALIFE, Inc., a complex of 1-MCP with alpha-cyclodextrin containing approximately 0.14 weight percent 1-MCP) in a 9:1 weight ratio. The resulting powder was compression molded at 140° C. to form a film, from which 11 mm×30 mm strips were cut, resulting in approximately 10 mg ETHYLBLOC per strip. The strips in Sample 2 were thicker than in Sample 1, thus resulting in approximately the same loading of ETHYLBLOC.

The release of 1-MCP from the resulting 1-MCP containing water-soluble films was compared to the release of 1-MCP from ETHYLBLOC powders. The analysis method used was head space analysis by gas chromatography using a flame ionization detector. The heater on the oven was turned off, with the temperature reading on the oven about 28-29° C. while room temperature was about 22° C.

The dimensions of the headspace vials were: 18 mm by 60 mm, with the opening at the neck of the vial being 12 mm. Therefore, samples were sized 11 mm×30 mm to fit. Each sample was prepared so that it contained about 10 mg of ETHYLBLOC. Sample testing was performed by either immersing the sample in water, or placing the sample in the presence of water vapor.

Release of 1-MCP from the powdered ETHYLBLOC, as a control sample, or from the film samples (Samples 1 and 2) by immersion of water was performed by immersing the samples (either 10 mg ETHYLBLOC or an 11 by 30 mm film) into water in a 22 mL headspace vial. The headspace vials were placed in the sampler oven, and the measurement was taken after 15 minutes.

For measuring the release of 1-MCP from the powdered ETHYLBLOC, as a control sample, due to exposure to humidity, 10 mg of ETHYLBLOC was weighed into a 22 mL headspace vial. Then 1.0 mL of water was dispensed into a 2 mL autosampler vial. The 2 mL vial with water was then lowered into the headspace vial with a pair of tweezers and the headspace vial was crimped closed. This procedure prevented immersion of the ETHYLBLOC in water, but because the 2 mL vial was not capped, the ETHYLBLOC would be exposed to the water vapor.

For measuring the release of 1-MCP from the films due to exposure to humidity, the film samples were placed into a 22 mL headspace vial. Then the 2 mL autosampler vial filled with 1 mL water was carefully lowered into the headspace vial with a pair of tweezers and the headspace vial was crimped closed. Care was taken to ensure that the sample did not directly contact any water. The headspace vials containing vapor samples were placed in the sampler oven, and the head space analysis measurement was taken after a given time period. Each vial was sampled once, that is a new vial was used to obtain each data point for time release studies.

The concentration of 1-MCP was estimated using cyclopentene to calibrate the detector. The procedure was to calibrate the gas chromatograph by preparing vials that contained 1-3 µL of a solution of 0.01 g/mL cyclopentene in hexane. This solution completely evaporates in the headspace vial at room temperature to give a known amount of cyclopentene vapor.

The head space analysis results are summarized in FIG. 1 and the Tables 1-4.

TABLE 1

Water Immersion Results.

| Sample | 1-MCP released, ppm/mg ETHYLBLOC |
|---|---|
| ETHYLBLOC (run #1) | 26 |
| ETHYLBLOC (run #2) | 28 |
| Sample 1 (3:1 POLYOX:ETHYLBLOC) | 19.6 |
| Sample 2 (9:1 POLYOX:ETHYLBLOC) | 9.8 |

TABLE 2

Humidity Exposure Results for ETHYLBLOC.

| Time (hours) | 1-MCP released, ppm/mg ETHYLBLOC |
|---|---|
| 0.25 | 0.3 |
| 0.5 | 0.4 |
| 24 (run #1) | 10.3 |
| 24 (run #2) | 9.3 |
| 43 (run #1) | 15.1 |
| 43 (run #2) | 15.8 |

TABLE 3

Humidity Exposure Results for Sample 1.

| Time (hours) | 1-MCP released, ppm/mg ETHYLBLOC |
|---|---|
| 1.5 | 2.7 |
| 24 (run #1) | 30.2 |
| 24 (run #2) | 32.2 |
| 48 | 20.7 |

TABLE 4

Humidity Exposure Results for Sample 2

| Time (hours) | 1-MCP released, ppm/mg ETHYLBLOC |
|---|---|
| 5 (run #1) | 2.2 |
| 5 (run #2) | 2.9 |
| 16 (run #1) | 29.5 |
| 16 (run #2) | 19.3 |
| 49 (run #1) | 27.9 |
| 49 (run #2) | 30.9 |

The above results indicate that forming a water-soluble film containing a 1-MCP complex may allow for the release of 1-MCP upon exposure to humidity or immersion in water. For exposure to humidity; the water soluble films containing the 1-MCP complex may release 1-MCP 1.5 to 2 times faster than the control samples of 1-MCP complex as a powder. Upon exposure to liquid water, the 1-MCP complex as a powder released the 1-MCP faster, however various formulations of films may provide for a faster release rate, thus providing the increased release rate, if desired, along with improved handling.

The use of a water soluble film directly incorporating the ethylene blocking agent complex may provide for a more convenient and efficient delivery, fewer processing steps, and increased control over ethylene blocking agent delivery as compared to the prior art, which uses the complex as a powder directly, compresses the powder into a tablet, encloses the powder inside a sachet made from water insoluble or soluble polymers, incorporates (as a complex or as 1-MCP gas) into a hydrophobic film, or incorporates the complex into a gel coating on an insoluble substrate. Additionally, films may provide for small-scale operations, including individual packaging.

Release of 1-MCP from a sachet was also investigated. A sachet was formed using a non-woven polypropylene fabric (non-woven material 5D49 PP, a porous thin sheet of spunbond homopolymer polypropylene, available from The Dow Chemical Co., Midland, Mich.). The non-woven sheets were cut into rectangular pieces 10 mm by 30 mm. Two of the pieces were placed on top of each other and folded in half, creating a double layered pocket (so as to minimize powder loss or exposure through a single-layered sachet). Two edges of the pocket were sealed with an IMPULSE sealer, then 10 mg of ETHYLBLOC was placed inside the pocket and the final edge sealed.

Head-space analyses were conducted for sachets immersed in water and exposed to humidity. When the sachets were immersed in water, more than 90 percent of the 1-MCP they contained was released. When exposed to humidity, 1-MCP release results are given in Table 5.

TABLE 5

Sachets exposed to humidity.

| Time (hours) | 1-MCP released, ppm/mg ETHYLBLOC |
|---|---|
| 4 (run #1) | 5.66 |
| 4 (run #2) | 6.14 |
| 48 (run #1) | 23.3 |
| 48 (run #2) | 23.3 |

Figure 2:
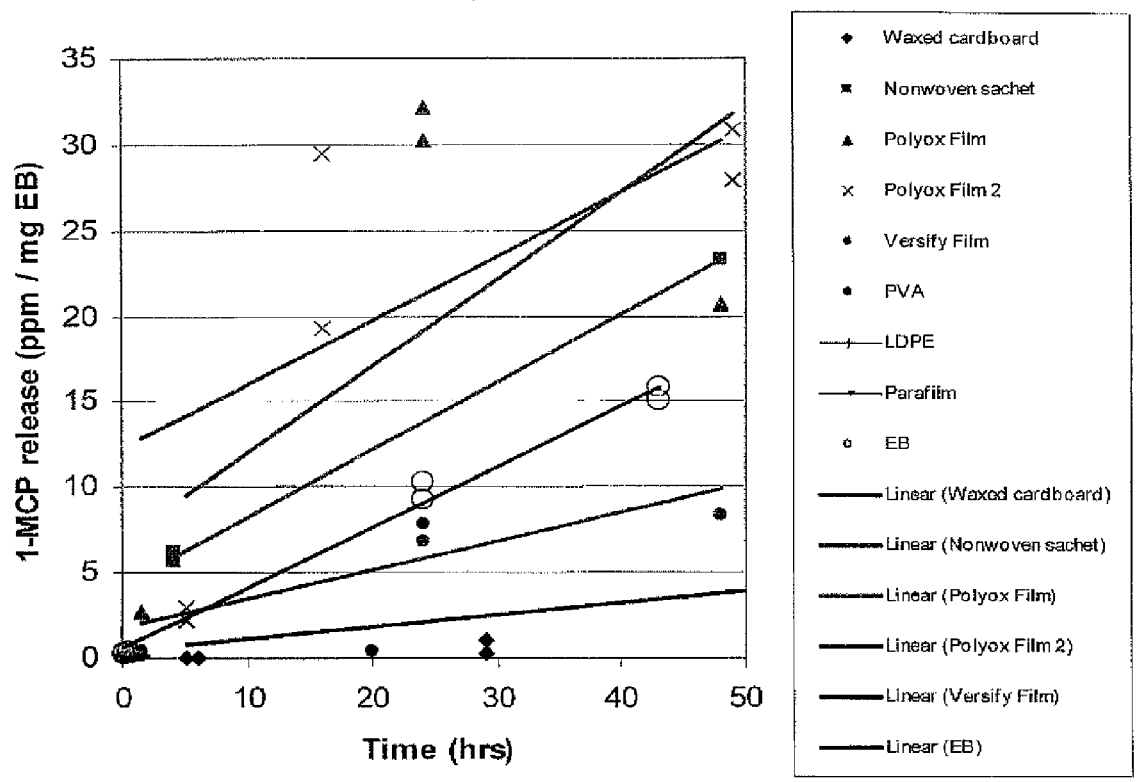
FIG. 2 graphically compares experimental results for release rates for various films, sachets, and substrates comprising or coated with compositions comprising 1-MCP according to embodiments disclosed herein.

FIG. 2 graphically illustrates experimental results for release rates for various films, sachets, and substrates comprising or coated with compositions comprising ETHYLBLOC ("EB") according to embodiments disclosed herein. These results illustrate several compositions, including water-soluble polymers (POLYOX films, poly(vinyl alcohol) films), as well as water-permeable substrates (non-woven sachet), among others, compared to release of 1-MCP from ETHYLBLOC ("EB") powders or tablets when exposed to humidity. These results indicate that polymer choice and delivery method are effective means to vary the time release characteristics of the ethylene blocking agent from the composition.

In generating the data for FIG. 2, the following materials were used:

Paraffin wax IGI 1240A was purchased from IGI, Inc. Non-woven material 5D49 PP was obtained from The Dow Chemical Company (Midland, Mich.). It is a porous thin sheet of a spunbond homopolymer polypropylene fabric, with the weight of the fabric per area 17 g/m2. POLYOX WSR N80 was obtained from The Dow Chemical Company (Midland, Mich.). VERSIFY DE2400 and AFFINITY 8150 polymers were obtained from The Dow Chemical Company (Midland, Mich.) as pellets.

The preparation of the prototypes was made under atmospheric conditions; a dry box was not used. Exposure of the ETHYLBLOC to water, humidity, and temperature was minimized by preparing the samples as quickly as possible and upon completion immediately storing in a sealed container containing room air.

Preparation of Wax-Coated Cardboard Prototypes:

0.13 g of solid paraffin wax was broken into small pieces and evenly distributed on a piece of corrugated cardboard, 10 mm×30 mm size. The cardboard sample was placed on a hot plate and heated to ca. 70° C. to allow paraffin to melt. 10 mg of ETHYLBLOC was then uniformly sprinkled on top of the melted paraffin, and the sample was removed from hot plate to cool.

Preparation of Sachets:

Non-woven sheets were cut into rectangular pieces of 10 mm×30 mm size. 2 of these pieces were placed on top of each other, and folded in half, to create double layered pocket. 10 mg of ETHYLBLOC was placed inside the pocket and the edges sealed with an Impulse sealer.

Preparation of Film Samples

Group 1

POLYOX WSR N80 polymer in a powdered form was thoroughly dry-mixed with ETHYLBLOC in 3:1 ratio. The resulting powder was compressed at 93° C. under pressure. The 10 mm×30 mm strips were cut from the resulting film.

VERSIFY DE2400 polymer in a pellet form was dry-mixed with ETHYLBLOC in 3:1 ratio. The resulting mixture was compressed at 93° C. under pressure. The 10 mm×30 mm strips were cut from the resulting film.

AFFINITY 8150 polymer in a pellet form was dry-mixed with ETHYLBLOC in 3:1 ratio. The resulting mixture was compressed at 140° C. under pressure. The 10 mm×30 mm strips were cut from the resulting film.

Group 2

POLYOX WSR N80 polymer in a powdered form was dry-mixed with ETHYLBLOC in 9:1 ratio. The resulting powder was compressed at 140° C. under pressure. The 10 mm×30 mm strips were cut from the resulting film.

VERSIFY DE2400 polymer in a pellet form was mixed with ETHYLBLOC in 9:1 ratio. The resulting mixture was compressed at 93° C. under pressure. The 10 mm×30 mm strips were cut from the resulting film.

AFFINITY 8150 polymer in a pellet form was dry-mixed with ETHYLBLOC in 9:1 ratio. The resulting mixture was compressed at 93° C. under pressure. The 10 mm×30 mm strips were cut from the resulting film.

All of these samples were immersed in water and the data recorded which form the basis of FIG. 2.

Advantageously, embodiments disclosed herein may provide for direct incorporation of the ethylene blocking agent complex into a water soluble film offering one or more of the following advantages (1) completely variable dosing, (2) easy and safe handling, and (3) optimal or controllable release characteristics. In some embodiments, for example, the user may simply tear off the needed amount and not be limited to discrete quantities (tablets, sachets, etc.). Incorporation of ethylene blocking agents, such as 1-MCP, into a film allows a slight delay in 1-MCP release as water initial penetrates the film. This is desired to minimize worker exposure both to the 1-MCP vapor and the ethylene blocking agent complex. Additionally, the large surface area provided by films may give a large ethylene blocking agent release once the film has been initially penetrated. The hydrophilic films may also enable faster release than a solid tablet or a hydrophobic film, transporting water to the complex without the need for additives. Additionally, films and other structures and substrates incorporating ethylene blocking agent complexes disclosed herein may provide for the desired ethylene blocking, and may obviate the need for a separate treatment step, such as warehouse fumigation.

Advantageously, water-soluble or partially water-soluble or water-swellable films may provide an alternative to handling powder or pellets directly. Additionally, water-soluble films may be sufficiently hydrophilic and of a sufficient aspect ratio that additives such as SAPs or effervescent ingredients may not be required to enhance the efficiency of the ethylene blocking agent release.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All priority documents are herein fully incorporated by reference for all jurisdictions in which such incorporation is permitted. Further, all documents cited herein, including testing procedures, are herein fully incorporated by reference for all jurisdictions in which incorporation is permitted to the extent such disclosure is consistent with the description of the present invention.

What is claimed:

1. A dispersion comprising:
    an ethylene blocking agent complex comprising the product of an ethylene blocking agent selected from the group consisting of cyclopropene, 1-methylcyclopropene, 3,3-dimethycyclopropene, methylenecyclopropane and derivatives thereof and a host selected from the group consisting of cyclodextrins and crown ethers; and
    at least one degradable polymer selected from the group consisting of polyesters, polyurethanes, polyethers, and polyanhydrides,
    wherein a ratio of degradable polymer to ethylene blocking agent complex is in the range from 1:1 to 1:9 by weight.

2. The dispersion of claim 1, wherein the ethylene blocking agent comprises 1-methylcyclopropene.

3. The dispersion of claim 1, wherein the degradable polymer comprises polyester resins obtained from the reaction of bisphenol A and propylene oxide followed by the reaction of the resulting product with fumaric acid.

4. The dispersion of claim 1, wherein the degradable polymer comprises the esterification products of a di- or polycarboxylic acid and a diol comprising a diphenol.

5. The dispersion of claim 1, wherein the degradable polymer comprises at least one functional group selected from the group consisting of ethylenically unsaturated mono- and di-functional carboxylic acids, ethylenically unsaturated mono- and di-functional carboxylic acid anhydrides, salts thereof and esters thereof.

6. The dispersion of claim 1, further comprising an ethylene generating agent.

7. The dispersion of claim 1, wherein the host comprises alpha-cyclodextrin.

8. The dispersion of claim 1, further comprising a water-insoluble polymer.

9. The dispersion of claim 8, wherein a ratio of degradable polymer to water-insoluble polymer is in the range from 50:1 to 1:50.

10. The dispersion of claim 1, wherein the ethylene blocking agent complex comprises from 0.05 to 0.5 percent by weight ethylene blocking agent.

11. The dispersion of claim 1, further comprising at least one of an herbicide, a fungicide, a growth factor, an insecticide, and a fertilizer.

12. The dispersion of claim 1, further comprising water.

13. The dispersion of claim 1, further comprising polyvinylpyrrolidone.

14. The dispersion of claim 1, further comprising at least one surfactant selected from the group consisting of polyoxyethylene sorbitan fatty acid esters, polyoxyethylene alkyl ethers, polyoxyethylene castor oil derivatives, propylene glycol, polyethylene glycol, or polyalcohols commonly used in food, food service, cosmetic, or pharmaceutical products, mono and diglycerides of fatty acids, and polyoxyethylene sorbitol esters.

15. The dispersion of claim 1, further comprising a thickener selected from the group consisting of silicon dioxide, xanthan gums, polyacrylamide polymers' and polyacrylamide gels, methylcellulose, and carboxyl methylcellulose.

16. A method of forming a dispersion comprising mixing;
(a) a dispersing medium comprising a mixture of at least one of water and solvent;
(b) an ethylene blocking agent complex comprising the product of an ethylene blocking agent selected from the group consisting of cyclopropene, 1-methylcyclopropene, 3,3-dimethycyclopropene, methylenecyclopropane and derivatives thereof and a host selected from the group consisting of cyclodextrins and crown ethers; and
(c) at least one degradable polymer selected from the group consisting of polyesters, polyurethanes, polyethers, and polyanhydrides
to form a dispersion,
wherein a ratio of degradable polymer to ethylene blocking agent complex is in the range from 1:1 to 1:9 by weight.

17. The method of claim 16 wherein mixing comprises melt kneading.

18. The method of claim 16 wherein mixing further comprises (d) a dispersion stabilizing agent.

19. The method of claim 16 wherein mixing further comprises (e) at least one of a frothing surfactant, an additive, and a filler.

* * * * *